United States Patent [19]

Huang et al.

[11] Patent Number: 5,468,898
[45] Date of Patent: Nov. 21, 1995

[54] SUBSTITUTED NAPHTHYLENE COMPOUNDS EXHIBITING SELECTIVE LEUKOTRIENE $B_4$ ANTAGONIST ACTIVITY

[75] Inventors: Fu-Chih Huang, Gwynedd; Wan K. Chan, Wayne; Charles A. Sutherland, Greenlane; Robert A. Galemmo, Jr., Collegeville, all of Pa.

[73] Assignee: Rhone-Poulenc Rorer Pharmaceuticals Inc., Collegeville, Pa.

[21] Appl. No.: 777,246

[22] PCT Filed: Sep. 6, 1991

[86] PCT No.: PCT/US91/06447

§ 371 Date: Apr. 23, 1993

§ 102(e) Date: Apr. 23, 1993

[87] PCT Pub. No.: WO92/04315

PCT Pub. Date: Mar. 19, 1992

Related U.S. Application Data

[63] Continuation-in-part of Ser. No. 580,243, Sep. 10, 1990, abandoned.

[51] Int. Cl.$^6$ ............... C07C 233/51; C07D 257/04
[52] U.S. Cl. ................ 560/41; 562/450; 548/253
[58] Field of Search ............... 548/253; 560/41; 562/450

[56] References Cited

U.S. PATENT DOCUMENTS

| | | |
|---|---|---|
| 2,692,882 | 10/1954 | Speeter . |
| 3,868,405 | 2/1975 | Brain et al. . |
| 4,814,463 | 3/1989 | Kim . |
| 5,015,657 | 5/1991 | Boshagen et al. . |

FOREIGN PATENT DOCUMENTS

| | | |
|---|---|---|
| 0276064 | 7/1988 | European Pat. Off. . |
| 0276065 | 7/1988 | European Pat. Off. . |
| 0292977 | 11/1988 | European Pat. Off. . |
| 2230349 | 12/1974 | France . |
| WO92/04315 | 3/1992 | WIPO . |
| WO92/05145 | 4/1992 | WIPO . |

Primary Examiner—David B. Springer
Attorney, Agent, or Firm—James A. Nicholson; Martin F. Savitzky; Raymond S. Parker, III

[57] ABSTRACT

This invention relates to bicyclic aryl compounds having selective $LTB_4$ antagonist properties and comprising an amido substituent, a substituent group having a terminal carboxylic acid or derivative thereof and a lipophilic substituent, and to methods for the treatment of disorders which result from $LTB_4$ activity and pharmaceutical compositions including such compounds.

6 Claims, No Drawings

SUBSTITUTED NAPHTHYLENE COMPOUNDS EXHIBITING SELECTIVE LEUKOTRIENE B₄ ANTAGONIST ACTIVITY

This application is a continuation-in-part application of U.S. Ser. No. 07/580,243 filed on Sep. 10, 1990, abandoned.

BACKGROUND OF THE INVENTION

1. Field of the Invention

The present invention relates to a class of novel compounds useful in the treatment of a variety of diseases that involve undesirable inflammatory or hypersensitivity responses in diverse animal tissues. Approaches to the treatment of these responses have been as varied as the tissues in which such responses take place, and include the administration of antihistamines, analgesics such as aspirin, topical coal tar as well as others.

A more recent approach to the moderation of inflammatory and hypersensitivity responses has focused on blocking the action of arachidonic acid metabolites (including the prostaglandins), lipoxygenases and the leukotrienes. The leukotrienes (LT) metabolites are formed by oxygenation of a lipoxygenase (5-hydroperoxy-tetraenoic acid (5-HPETE)) which is formed by the specific oxygenation of the C-5 position of arachidonic acid. The first leukotriene formed in the metabolic pathway is the unstable epoxide intermediate leukotriene $A_4$ ($LTA_4$) which is the precursor to the family of peptido-leukotrienes, the first in the pathway being $LTC_4$ which is formed by glutathione addition. $LTC_4$ is transformed subsequently into $LTD_4$ and $LTE_4$ by successive elimination of a glutamyl and glycine residue. The peptido-leukotrienes primarily act on smooth muscle and other cells having contractile capacity, as well as playing a key role in hypersensitivity reactions. In addition, the peptido-leukotrienes are spasmogens, increase vascular permeability, activate airway smooth muscle, stimulate mucous secretion and are involved with the pathogenesis of certain inflammatory diseases such as bronchitis, ectopic and atopic eczema and psoriasis. Leukotrienes appear to be involved in the pathogenesis of asthma such as allergic pulmonary disorders of asthma, hay fever and allergic rhinitis. In addition, $LTC_4$, $LTD_4$ and $LTE_4$ may also decrease blood pressure by an action on the heart, because they reduce myocardial contractility and coronary blood flow.

Another family of leukotrienes, $LTB_4$, is derived from $LTA_4$ by hydrolase-catalyzed addition of water. This 5, 12-dihydroxy derivative causes adhesion and chemotactic movement of leukocytes, stimulates aggregation, enzyme release and generation of superoxide in neutrophils. Additionally, LTB4 is a potent chemotactic and chemokinetic agent for eosinophils, macrophages and monocytes, stimulates suppressor T lymphocytes and enhances natural cytotoxic cell activity. $LTB_4$ is also a potent (indirect) bronchoconstrictor but in contrast to the peptido-leukotrienes $C_4$, $D_4$ and $E_4$ does not appreciably stimulate mucous production and induce edema of the airways by increasing vascular permeability.

2. Reported Developments

It has been suggested that compounds antagonizing $LTB_4$ activity may be valuable in the treatment of inflammatory diseases caused by tissue degrading enzymes and reactive chemicals liberated by tissue-infiltrating and aggregating polymorphonuclear leukocytes. Such disease states include inflammatory bowel disease, reperfusion injury, chronic lung diseases, various arthritic conditions, inflammatory conditions associated with asthma (such as late phase hypersensitivity) and psoriasis.

The literature reports a variety of compounds exhibiting leukotriene $B_4$ antagonist activity. These include compounds having chemical structures mimicking leukotriene structures such as Sumitomo's SM 9064, UpJohn's U-75360 and U-75302 and Ciba Geigy's CGS 23113. Other compounds, some of which include monocyclic ring structures and which are disclosed in EP 276064, EP 276065 and EP 292977, are reported to exhibit both $LTD_4$ and $LTB_4$ antagonist properties.

The present invention is directed to a class of novel bicyclic ring containing compounds which exhibit selective $LTB_4$ antagonist activity.

SUMMARY OF THE INVENTION

This invention relates to compounds having $LTB_4$ antagonist properties and to therapeutic compositions and methods for the treatment of disorders which result from $LTB_4$ activity. In general, this invention comprises bicyclic aryl compounds having selective $LTB_4$ antagonist properties and comprising an amido substituent, a substituent group having a terminal carboxylic acid or derivative thereof and a lipophilic substituent.

DETAILED DESCRIPTION OF THE PREFERRED EMBODIMENTS

As employed above and throughout this disclosure, the following terms, unless otherwise indicated, shall be understood to have the following meanings:

"Bicyclic aryl" means a bicyclic ring system composed of two fused rings which may be partially or completely unsaturated carbocyclic and/or heterocyclic rings. Preferred bicycles include naphthalene, indole, benzothiophene, benzofuran, quinoline, chromone and purine.

"Monocyclic aryl" means a partially or completely unsaturated carbocyclic or heterocyclic ring. Preferred monocycles include benzene, thiophene, pyridine, furan and pyrimidine.

"Aryl" refers to a partially or completely unsaturated carbocyclic or heterocyclic aromatic ring.

"Alkyl", either alone or with various substituents defined herein, means a saturated aliphatic hydrocarbon, either branched- or straight-chained. A "loweralkyl" is preferred having about 1 to about 6 carbon atoms. Examples of alkyl include methyl, ethyl, n-propyl, isopropyl, butyl, sec-butyl, t-butyl, amyl and hexyl.

"Alkoxy" refers to a loweralkyl-O-group.

"Alkenyl" refers to a hydrocarbon having at least one point of unsaturation and may be branched- or straight-chained. Preferred alkenyl groups have 2 to about 6 carbon atoms present. Exemplary alkenyl groups include vinyl, allyl, ethynyl and isopropenyl.

The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

"Halo" means a halogen. Preferred halogens include chloride, bromide and fluoride. The preferred haloalkyl group is trifluoromethyl.

More specifically, the bicyclic 6,6 and 6,5 aryl ring systems are preferred. These are described by formulae I and II

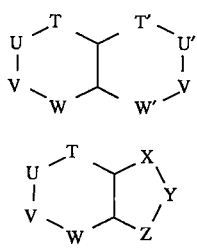

Formula I

Formula II where T, U, V and W and T', U', V' and W' are selected from $CR_1R_2$, $NR_3$, O and S provided that each ring of said bicyclic systems contain 0–2 hetero atoms and said hetero atoms are not vicinal oxygen and/or sulfur atoms;

X and Z are independently $CR_1R_2$, $NR_3$, O or S;

Y is $CR_1R_2$ or $NR_3$; and $R_1$ is hydrogen, alkyl or together with a vicinal $R_1$ may form a carbon-carbon double bond or together with a vicinal $R_3$ may form a carbon-nitrogen double bond. $R_1$, $R_2$ and $R_3$ are further described below.

Preferred bicyclic ring systems include indene, isoindene, benzofuran, benzothiophene, indole, 1H-indazole, indoline, benzopyrazole, benzoxazole, purine, naphthalene, tetralin, coumarin, chromone, quinoline, isoquinoline, quinazoline, pyrido[3,4-b]pyridine and 1,4-benzisoxazine.

Still more preferred compounds are described by Formula II where T, U, V and W are $CR_1R_2$ or $NR_3$ and T+U+V+W contain no more than 2 $NR_3$ groups.

Turning now to the three substituents which are necessarily attached to the bicyclic ring system, the preferred first substituent, which we have called the amido function, may be described by formula III:

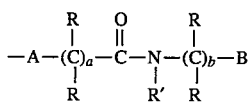

Formula III

The preferred second substituent having a terminal carboxylic acid or derivative thereof may be described by formula IV:

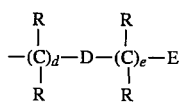

Formula IV

The preferred third substituent, the lipophilic substituent, may be described by formula V:

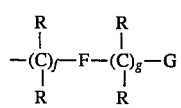

Formula V where A, B, D, E, F, G, R, R', a, b, d, e, f and g are as described below.

These above substituents of formulae III to V may be attached at various positions of the bicyclic ring system and therefore they form part of the definition for both $R_2$ and $R_3$ and could be present at such sites of the bicyclic ring systems defined as $CR_1R_2$ or $NR_3$. When $R_2$ and $R_3$ are neither substituent described by Formulae III to V, $R_2$ may further be selected from hydrogen, alkyl, alkenyl, aryl, aralkyl, alkoxy, aryloxy, aralkoxy, amino, mono- and dialkylamino, mercapto, alkylthio, aralkylthio, nitro, halo or haloalkyl;

geminal $R_1$ and $R_2$ may be =O; and $R_3$ may further be selected from hydrogen or alkyl.

The following definitions apply to the substituents of formulae III to V, each of which is attached at a suitable position on the bicyclic ring, where:

A is —CRR, O, S, NR', SO or $SO_2$;

B and G are each independently a substituted or unsubstituted monocyclic or bicyclic aryl;

D and F are each independently a bond O, S, NR', SO, $SO_2$, CONR', NR'CO, —CRR, —O—(CRR)$_j$—, —(CRR)$_j$—O—, —O—(CRR)$_j$—CR=CR—, —CR=CR—(CRR)$_j$—O— where j is 1–4 or (CR=CR)$_x$ where x is 0–2 or C≡C;

E is —COOR', —CONR'R',

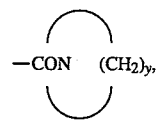

where y is 2–5, —CN, —CONHSO$_2$R',

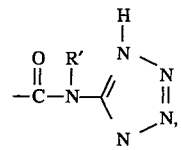

tetrazolyl or substituted tetrazolyl where the substituent is alkyl, carboxyalkyl or carbalkoxyalkyl;

R is independently hydrogen or —(CH$_2$)$_m$—R$_2$ where m is 0–5 or together with a vicinal R group or vicinal R' group forms a 4–7 membered ring which may be saturated or partially unsaturated;

R' is hydrogen, alkyl or aralkyl; and a, b, d, e, f and g are 0–4 provided d+f+g+x≠0.

The most preferred compounds of this invention are described by those compounds of formula II where:

X, Y and Z are $CR_1R_2$ or $NR_3$ provided at least one of X, Y and Z is $CR_1R_2$;

T, U, V and W are $CR_1R_2$ or $NR_3$ provided at least two of T, U, V and W are $CR_1R_2$;

$R_1$ is hydrogen or together with a vicinal $R_1$ may form a carbon-carbon double bond or together with a vicinal $R_3$ may form a carbon-nitrogen double bond;

$R_2$ and $R_3$ are independently hydrogen, and at least one of $R_2$ and $R_3$ is

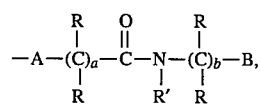

at least another of $R_2$ or $R_3$ is

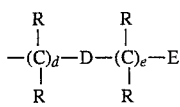

and at least one other of $R_2$ and $R_3$ is

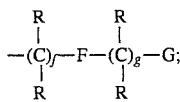

where A, B, D, E, F, G, R, R', a, b, d, e, f and g are as described above; and pharmaceutically acceptable salts thereof.

B and/or G may be optionally substituted with 1 to about 3 R" groups where R" is alkyl, haloalkyl, alkoxy, halo or nitro.

A special embodiment of this invention encompasses the compounds of formulae VIa and VIb.

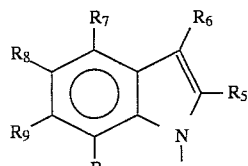
Formula VIa

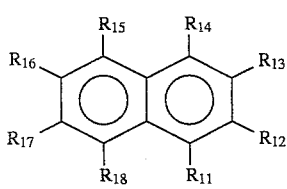
Formula VIb where at least one of $R_4$, $R_5$, $R_6$, $R_7$, $R_8$, $R_9$ and $R_{10}$ and $R_{11}$, $R_{12}$, $R_{13}$, $R_{14}$, $R_{15}$, $R_{16}$, $R_{17}$, $R_{18}$ are

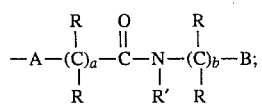

at least one of $R_4$, $R_5$, $R_6$, $R_7$, $R_8$, $R_9$ and $R_{10}$ and $R_{11}$, $R_{12}$, $R_{13}$, $R_{14}$, $R_{15}$, $R_{16}$, $R_{17}$ and $R_{18}$ are

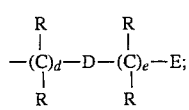

and at least one of $R_4$, $R_5$, $R_6$, $R_7$, $R_8$, $R_9$ and $R_{10}$ and $R_{11}$, $R_{12}$, $R_{13}$, $R_{14}$, $R_{15}$, $R_{16}$, $R_{17}$ and $R_{18}$

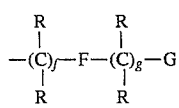

and the remaining $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$ and $R_{18}$ groups are hydrogen and where:

A is —CRR or O;

B and G are independently phenyl or substituted phenyl where the substituents are alkyl, haloalkyl, alkoxy or halo;

D is a bond, O, —CRR, —O—$(CRR)_j$—, —$(CRR)_j$—O—, —O—$(CRR)_j$—CR=CR—, —CR=CR—$(CRR)_j$—O— where j is 1–4 or —$(CR=CR)_x$ where x is 1 or 2;

E is —COOR', —CONR'R',

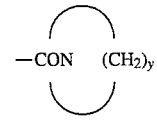

where y is 2–5 —CN, —CONHSO$_2$R',

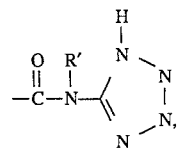

tetrazolyl or substituted tetrazolyl where the substituent is alkyl, carboxyalkyl or carbalkoxyalkyl;

F is a bond, O, —CRR, —NR'—$(CR=CR)_x$ where x is 0–2;

R is hydrogen or —$(CH_2)_m$—$R_2$ where m is 0–5;

$R_2$ is hydrogen, alkyl, alkenyl, phenyl, alkoxy, amino, mono- and di-alkylamino, mercapto, alkylthio, halo or haloalkyl;

R' is hydrogen, alkyl or aralkyl; and a, b, d, e, f and g are independently 0–4.

The preferred positions for substitution in the indole molecule of formula VI are the 1, 3, 4 and 5 positions, and the more preferred aspect of this special embodiment includes those compounds where:

A is CHR or O;

B and G are phenyl or substituted phenyl where the substitutents are loweralkyl or loweralkoxy;

D is a O, —CHR, —O—$(CRR)_j$—, —$(CRR)_j$—O—, —O—$(CRR)_j$—CR=CR—, —CR=CR—$(CRR)_j$—O— where j is 1–4 or $(CR=CR)_x$ where x is 1 or 2;

E is —COOR' or tetrazolyl;

F is a O or —CHR;

R is hydrogen, loweralkyl or aryl;

R' is hydrogen, loweralkyl or arloweralkyl; and a, b, d, e, f and g are independently 0–4.

Among the most preferred amido substituents are:

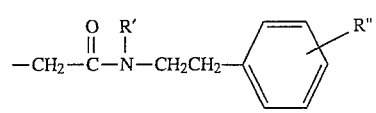

and

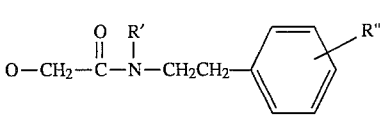

where R' is hydrogen or lower alkyl and R" is hydrogen, lower alkyl or lower alkoxy.

Among the most preferred terminal acidic substituents are: —(CRR)$_d$—(CRR)$_e$—E where d and e are 0–4, —(CR=CR)$_x$—E where x is 1–2, —O—(CRR)$_j$—(CRR)$_e$—E where j and e are 1–4, —O—(CRR)$_j$—CR=CR—E where j is 1–4 and R is hydrogen or lower alkyl and E is —COOH or

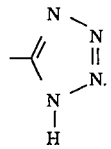

Among the most preferred lipophilic substituents are:

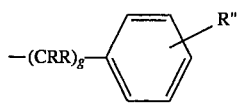

and

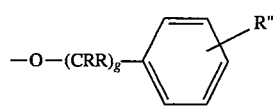

where g is 0–4 and R is hydrogen or lower alkyl and R" is hydrogen, lower alkyl or lower alkoxy.

While this invention necessitates the presence of three substituents attached to the bicyclic ring system as described by formulae III to V, it is often desirable to have a fourth substituent present. This may be the same or different as these already present or it may also be derived from formulae III to V. Other substituents may likewise be desired. It is to be understood that such compounds fall within the scope of this invention.

It may be of interest to one skilled in the art that compounds where E is OR' may also be of value as LTB$_4$ antagonists.

The compounds of this invention may be prepared by employing art recognized procedures from known compounds or readily preparable intermediates. Exemplary general procedures are as follows:

Since the compounds of this invention have three substituents which are necessarily present, the introduction of each substituent to the aryl ring system is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the bicyclic ring system involved.

It is convenient to synthesize these molecules by employing condensation reactions at reactive A, D and F cites of the molecule. Exemplary general procedures are as follows and are shown for convenience using the indole ring system. Of course, while the following reactions involved are basic to developing indole molecules having the three required substituents present, the substitution patterns for other bicyclic rings, such as napthalene, would depend on the chemistry of the particular ring. Any such adjustments to the chemistry would be familiar to one skilled in the art.

Thus, in order to prepare those compounds where A, D or F is O, S or NR' the following reactions or combination of reactions may be employed:

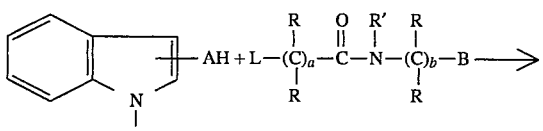

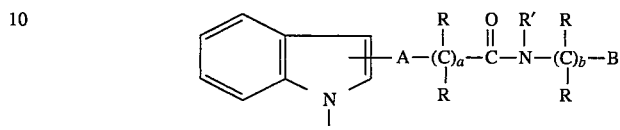

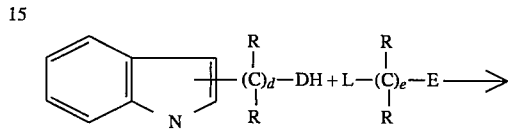

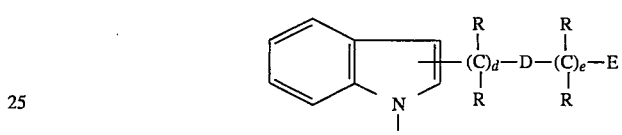

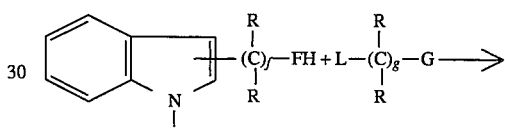

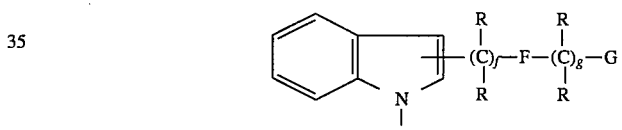

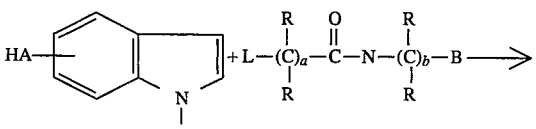

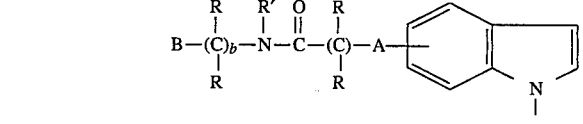

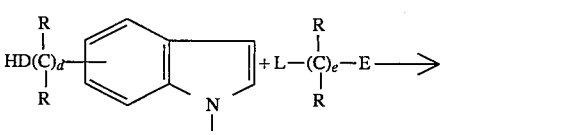

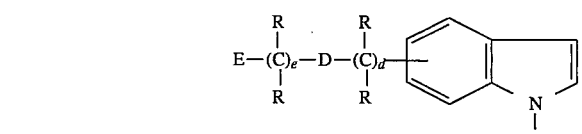

-continued

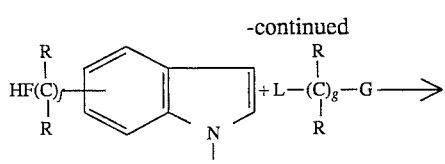

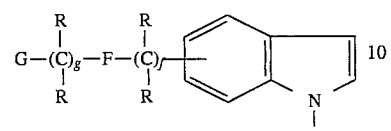

When A, D or F is O or S, the compounds may be prepared by condensation of a bicyclic aryl alcohol or thiol with a compound of the formulae

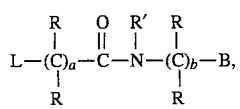

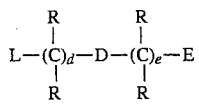

or

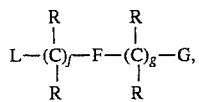

where E is preferably a nitrile, ester or tetrazole and L is a leaving group such as halo, tosylate or mesylate. This reaction is usually carried out in the presence of any base normally employed to deprotonate an alcohol or thiol such as sodium hydride, sodium hydroxide, triethyl amine, sodium bicarbonate, diisopropyl/ethylamine or methyl magnesium halides.

Reaction temperatures are in the range of room temperature to reflux and reaction times may vary from 2 to 96 hours. The reaction is usually carried out in a solvent that will dissolve both reactants and is inert to both as well. Solvents include, but are not limited to diethyl ether, THF, N,N-dimethyl formamide, dimethyl-sulfoxide, dioxane and the like.

When A is an alkyl group, it is convenient to prepare these compounds by Friedel-Crafts alkylation or by the Wittig reaction followed by reduction.

In the case where A, D or F is SO or $SO_2$, then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating with 30% $H_2O_2$.

Those compounds where F and/or D are

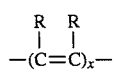

where x is 1 or 2, are prepared by reacting the appropriate aldehyde or ketone with an appropriate Wittig reagent or modified Wittig reagent of the formula

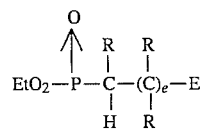

or

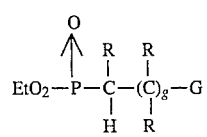

where E is cyano or carbalkoxy. Thus for example

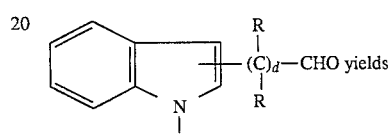

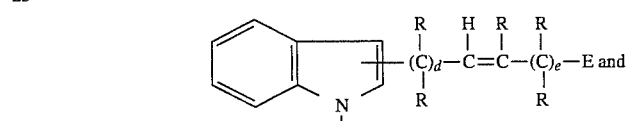

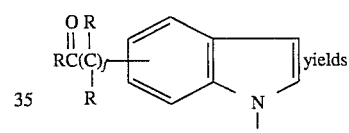

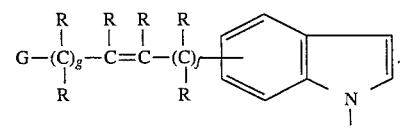

Reference for the Wittig reaction and modified Wittig reaction to control the formation of the trans and cis configuration at the double bond and the isomerization of cis and trans isomers can be found in A. Maercher, *Organic Reactions*, 14, 270, 1965.

The intermediate aldehyde compounds may be prepared in the usual manner from the corresponding carboxylic acid with an alkyllithium reagent, or from the oxidation of the corresponding alcohol. The aldehyde can also be obtained by Friedel-Crafts acylation or formylation ($POCl_3$/DMF) of the indole, etc.

When F and/or D are

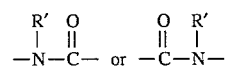

then the condensation of an acid or an acid halide with the appropriate aryl amine will give the desired compound.

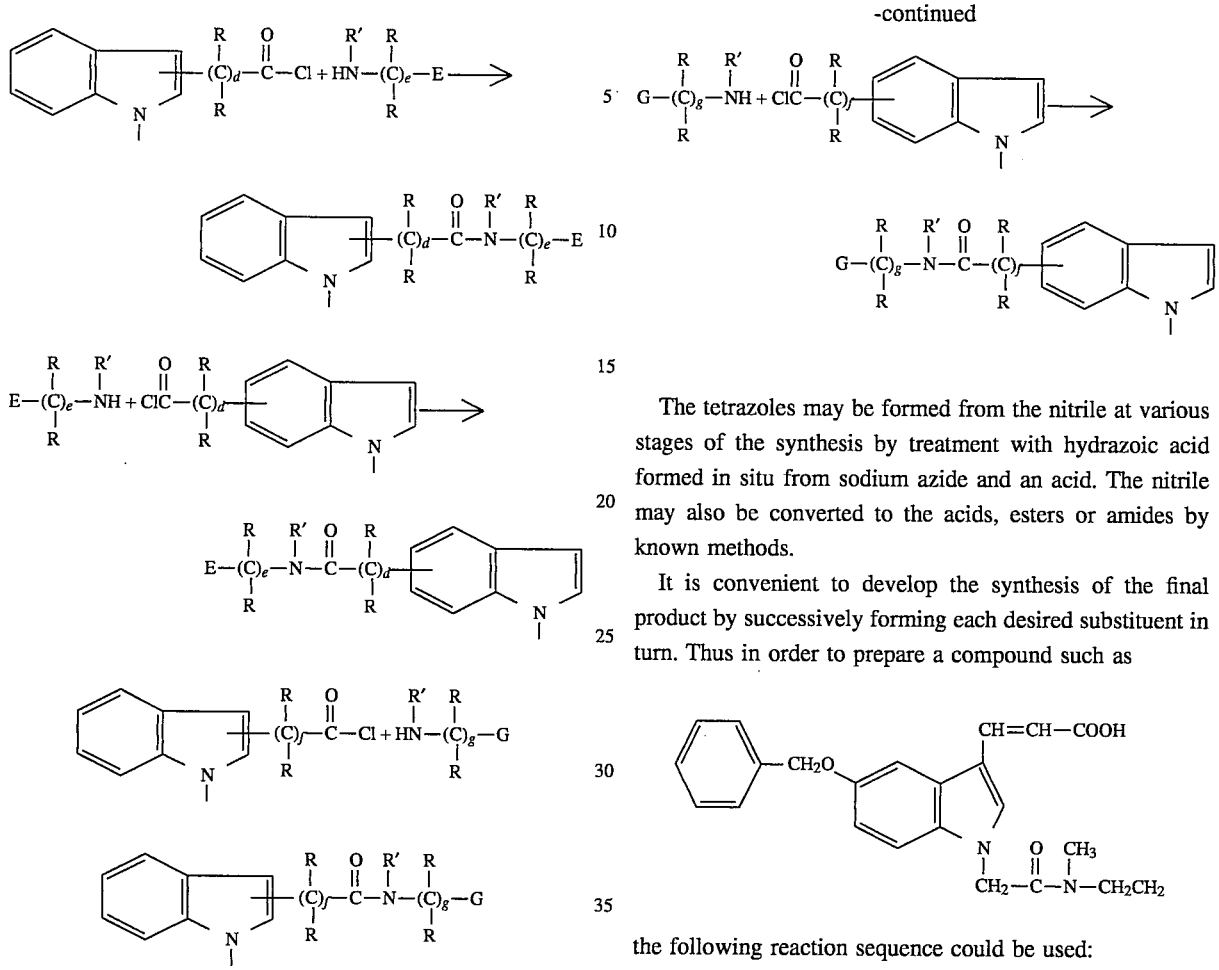

The tetrazoles may be formed from the nitrile at various stages of the synthesis by treatment with hydrazoic acid formed in situ from sodium azide and an acid. The nitrile may also be converted to the acids, esters or amides by known methods.

It is convenient to develop the synthesis of the final product by successively forming each desired substituent in turn. Thus in order to prepare a compound such as

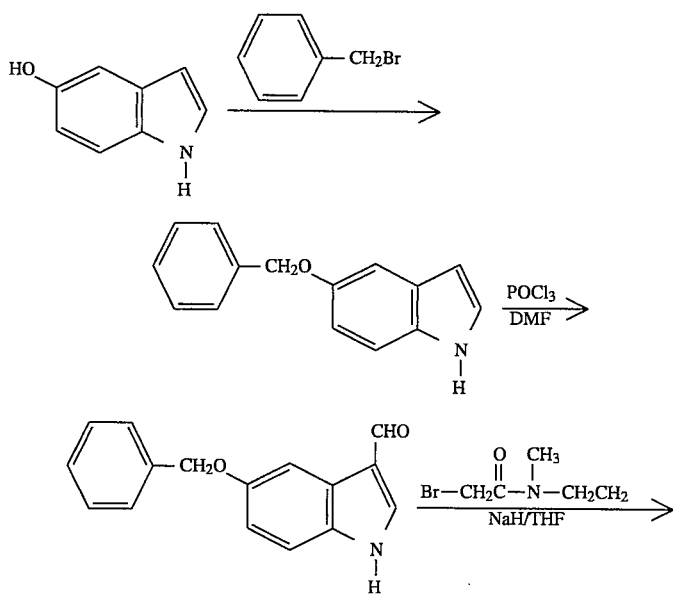

the following reaction sequence could be used:

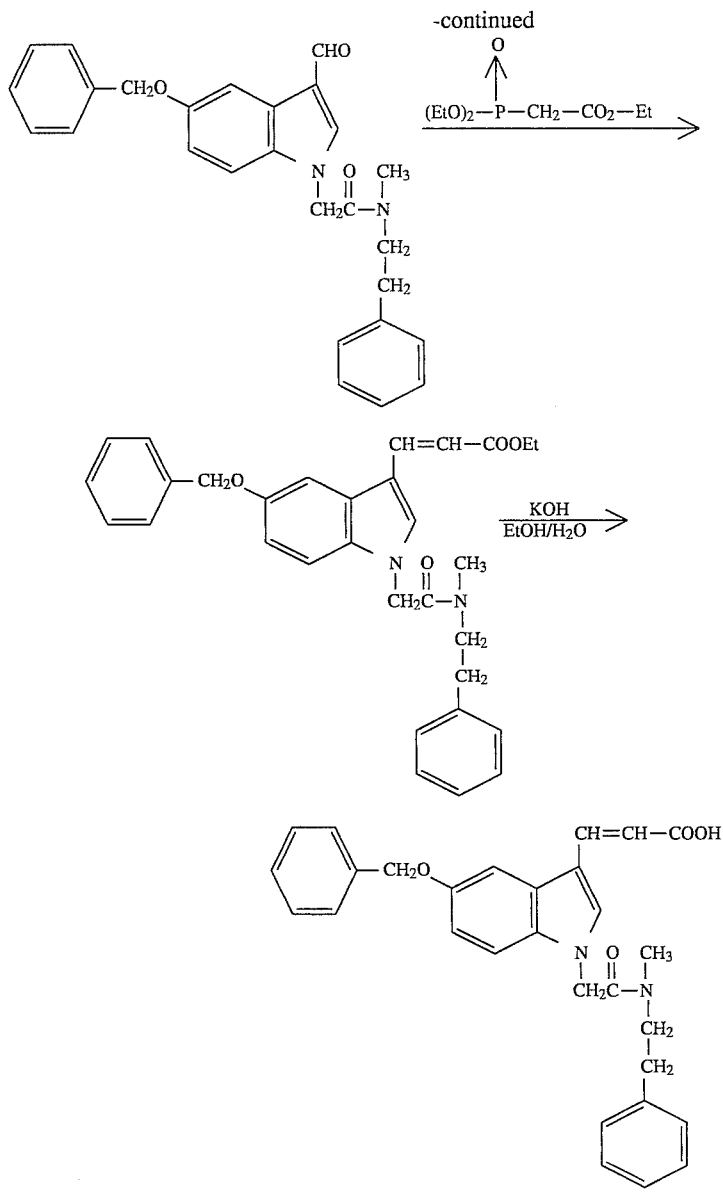

Certain compounds of this invention may have at least one asymmetric carbon atom such as those compounds having different geminal R groups. Further, certain compounds of this invention may exist in their cis or trans configuration such as those compounds where D and/or F is CR CR. As a result, those compounds of this invention may be obtained either as racemic mixtures, diastereoisomeric mixtures or as individual enantiomers. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al, J. Am. Chem. Soc. 96, 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds*: Optical Resolution Information Center, Manhattan College, Riverdale, N.Y. Such procedures are useful in the practice of this invention. A further useful reference is *Enantiomers, Racemates and Resolutions*: Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds, e.g., as defined in $R_2$ and R" can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then by transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Compounds within the scope of the present invention have potent activity as leukotriene $B_4$ antagonists and as such possess therapeutic value in the treatment of inflammatory conditions and hypersensitivity responses. $LTB_4$ is implicated in diseases such as rheumatoid arthritis, gout, psoriasis and inflammatory bowel disease and therefore compounds which demonstrate $LTB_4$ antagonist properties would be of valuable in the control of these states.

The $LTB_4$ guinea pig polymorphonuclear membrane binding assay can be used to determine compounds exhibiting $LTB_4$ receptor binding properties. Compounds active in this assay can then be subjected to the guinea pig peritoneal PMN $LTB_4$-induced aggregation assay. THE $LTB_4$-induced aggregation assay determines the antagonistic activity of a compound. The guinea pig $LTB_4$-induced wheal assay is used to determine in vivo activity.

Assay for Inhibitors of ($^3$H)-$LTB_4$ Binding to Membranes From Guinea Pig Polymorphonuclear Leukocytes Preparation of test compounds Dissolve compounds to a concentration 100-fold higher than the highest desired concentration for testing. Serially dilute the compound so that all dilutions are 100-fold higher than the assay concentration desired. Compounds are typically dissolved in DMSO. If compounds are insoluble in DMSO, solutions are heated or sonicated to induce solubilization. Compounds may also be dissolved in ethanol.

Final assay concentrations of DMSO and ethanol can be as high as 1.0% and 2.0% (v/v); these concentrations have no measurable effects on specific binding.

Preparation of the membrane receptor fraction

To obtain polymorphonuclear leukocytes (PMNs), 25–30 male Hartley guinea pigs (250–350 g) are intraperitoneally injected with 6 mls of an 8% sodium caseinate solution. 18 to 24 hours later, the guinea pigs are sacrificed by decapitation. The peritoneal cavity is lavaged with 15 mls of isolation buffer. The cells are collected and centrifuged at 200×g for 10 minutes. Contaminating red blood cells can be removed by hypotonic lysis. The cells are resuspended in isolation buffer and centrifuged as before. They are filtered through gauze and centrifuged again. The resulting pellet is suspended in 3 ml of sonication buffer, counted and brought to a concentration of $1 \times 10^8$ cells/ml. This suspension is lysed on ice with 5 bursts of 30 seconds separated by 1 minute intervals. The homogenate is centrifuged at 200×g for 10 minutes at 4° C. Aliquots of supernatant are transferred to high speed centrifuge tubes (1 tube per 3 guinea pigs). The tubes are centrifuged at 49,000×g for 15 minutes at 4° C. The pellets are resuspended by three 5 second bursts of sonication, separated by 20 second intervals. This suspension is centrifuged at 50,000×g for 20 minutes at 4° C. Pellets are stored at −70° C. for up to 3 months.

To use in the binding assay, the pellet is thawed at room temperature and suspended in 9 mls of assay buffer (sonication may be necessary).

Binding assay

Each assay tube (16×100 mm) contains the following:

345 µl Assay Buffer

5 µl Test compound or solvent

50 µl $^3$H-$LTB_4$ (0.50 nM)

100 µl Protein preparation (0.2 mg)

Incubations are done at 30° C. for 40 minutes in a water bath. Reactions are started by the addition of ($^3$H)-$LTB_4$ solution. Samples are collected via a Brandel M24 Harvester for binding assays. Tubes should be washed with a total of 19 ml cold wash buffer.

The filters are transferred to 7 ml plastic scintillation vials to which 6.0 ml of appropriate scintillation fluid (e.g., Scintiverse®) is added. After being allowed to equilibrate for 12 hours, the radioactivity is counted with a liquid scintillation counter appropriately set for tritium.

The required control assay tubes include the following:

(a) Total Binding: No test compound is added; buffer is substituted.

(b) Non-Specific Binding: Non-labeled ligand is added at a concentration of 1 µM.

(c) Solvent Controls: If test compound is dissolved in a solvent, controls for both Total Binding and Non-Specific Binding containing solvent but no compounds are required.

Calculations:

Specific binding is defined as that amount of radioligand prevented from binding by 1000-fold excess non-labeled ligand, i.e., total binding minus non-specific binding. This operational definition is verified by Scatchard analysis of total binding.

Inhibition of specific binding is defined as the decrease in specific binding caused by the test compound, $$\frac{SB_C - SB_T}{SB_C} \times 100$$

where $SB_C$ is the specific binding in the absence of test compound and $SB_T$ is the specific binding in the presence of test compound. The $I_{50}$ values (concentrations required to inhibit specific binding by 50%) are determined by graphic analysis of the specific binding observed in the presence of various concentrations of test compound.

The results of this test indicate that compounds of this invention exhibit valuable $LTB_4$ receptor binding properties which are useful in the treatment of inflammatory conditions and hypersensitivity responses.

LTB$_4$-Induced Wheal Formation in Guinea Pig

LTB$_4$ plays the role of a mediator in cellular induced inflammation. The induction of chemokinesis and chemotaxis of PMNs and macrophage by LTB$_4$ have contributed to its association with the vascular aspects of acute inflammatory reactions.

In this test intradermal injection of 0.1 ml of a 10 µg/ml solution of LTB$_4$ to guinea pig back skin causes the formation of a wheal. This wheal is visualized by the prior intravenous injection with the indicator 1% Evan's Blue dye. Following a 2 hour incubation post-LTB$_4$ challenge, the guinea pigs are euthanized via CO2 asphyxiation. Their dorsal skins are reflected and the diameters of the challenged sites are compared with those of the vehicle control injected sites.

Preparation and handling of guinea pigs

The guinea pigs must be quarantined 5 to 7 days prior to the study. The day before the test, the back and hind limbs are shaved taking care not to nick the skin. After shaving, the guinea pigs are fasted, but water is provided.

On the day of the test, the guinea pigs are weighed and identified with an ink mark designating them with numbers 1 through 5 in each group. Groups are formed by random distribution.

Preparation and route of administration of compounds

The oral vehicles are Polyethylene Glycol (PEG 400) (2 ml/kg) and methocel (0.5% w/v) (10 ml/kg). Exposure to the ultrasound of a Branson sonicator assures uniformity of suspension or dissolution of the test compounds. Compounds for parenteral administration are dissolved in saline with the assistance of 0.1N HCl and 0.1N NaOH and then adjusting the pH to near neutrality.

Although test compounds are usually administered orally, other routes of administration such as intravenous, intraperitoneal or subcutaneous may be Preparation of leukotriene B$_4$ for intradermal injection used.

LTB$_4$ is obtained as a stock solution (50 µg/ml) in ethanol and is stored at −80° C. until required for use. The stock solution or an appropriate aliquot is transferred from the ampule into a 10 ml glass vial using a pasteur pipette. The stock solution is then evaporated to dryness under a slow, steady stream of argon gas.

A solution of freshly prepared 0.25% Bovine Albumin in Phosphate-Buffered Saline is bubbled with argon gas until the saturation point is reached (approximately 5 minutes). This argon-saturated vehicle is then used to reconstitute the evaporated LTB$_4$ stock residue to yield a final working concentration of 10 µg/ml. The rubber stoppered vial of LTB$_4$ working solution is kept on wet ice during the study.

Preparation of Evan's Blue dye solution

Because Evan's Blue is an easily visible marker that binds to the plasma proteins, it has been selected to assist the investigator in the measurement of the wheals induced during the study. Evan's Blue Dye is dissolved as a 1% w/v solution in 0.9% w/v physiologic saline. The number of 1 ml plastic disposable syringes, fitted with 27 gauge, ½ inch needles and filled with the 1% dye solution, is determined by the number of animals expected to be included in the study.

Conduct of an experiment

Test compounds or their appropriate controls are administered orally with 16 gauge, 3 inch dosing cannulas. Immediately after dosing, the guinea pig is injected intravenously with 1 ml of 1% Evan's Blue Dye into a digital vein in the left or right shaved hind limb. This injection is facilitated best through the use of a 1 ml plastic syringe fitted with a 27 gauge, ½ inch needle. Immediately following Evan's Blue injection, the guinea pig is injected intracutaneously at each of 2 sites in the shaved dorsal midline with 0.1 ml of the prepared argon-saturated LTB$_4$ solution (1 µg/0.1 ml). A third site is intracutaneously injected with the argon-saturated 0.25% bovine albumin in phosphate-buffered saline to serve as a vehicle control.

2 hours after challenge, the guinea pigs are euthanized by inhalation of carbon dioxide. Carbon dioxide is administered by inserting a rubber tube from the tank into a plastic bag containing the caged group of guinea pigs. Asphyxiation occurs in approximately 5 minutes.

After death, the dorsal skins are reflected to enable the measurement of 2 perpendicular diameters of the resultant wheals. The area of each wheal is determined using the formula: Area=$\pi r^2$.

Calculations and statistics

For each guinea pig, the mean of the wheal areas obtained for the 2 injections sites is established after correction is made for the effect of the wheal area induced by the 0.25% Bovine Albumin in Phosphate-Buffered Saline vehicle. Then, a mean area for each treatment group with its corresponding standard error is calculated.

The following equation is used to calculate the percent inhibition of vehicle treated control wheal area by treatment with test compound:

$$\frac{\text{Mean Wheal Area}_{(Control)} - \text{Mean Wheal Area}_{(Treated)}}{\text{Mean Wheal Area}_{(Control)}}$$

In multiple dose experiments, the dose of a test compound that will cause 50% inhibition (ED$_{50}$) can be calculated from the regression equation for the response as percent inhibition (y) and log dose (x) and estimating the (ED$_{50}$) from: $\hat{y}(50)=bx+m$ where:

$\hat{y}$=50% inhibition, x=dose of test compound, b=slope of dose response line and m=intercept of the dose response line.

95% confidence limits of ED$_{50}$ are calculated from the regression equation by the method of Litchfield and Wilcoxon where:

$$ED_{25} = \hat{y}(25) = bx + m,$$

$$ED_{75} = \hat{y}(75) = bx + m \text{ and}$$

$$S = \frac{(ED_{75}/ED_{50}) + (ED_{50}/ED_{25})}{2}$$

where S is the slope function used to compute the limit factor fED$_{50}$ 2.77/$\sqrt{N}$ as fED$_{50}$=S. 2.77 is an estimator, N is the square root of the number of animals used for all the doses and fED$_{50}$ is the factor to determine the upper (RU) and lower (RL) limits of the ED$_{50}$ as: RU=ED$_{50}$×fED$_{50}$ and RL=ED$_{50}$÷fED$_{50}$. Statistical significance of any inhibition caused by treatment with a test compound can be calculated by applying Student's t (two-tailed) to the data.

Validation and specificity studies

The 1 µg/0.1 ml/site challenge dose of LTB$_4$ was selected for the reproducibility, sensitivity and ease of measurement of the resultant wheal. Studies have indicated that size of wheals induced by LTB$_4$ is directly related to the dose administered.

2 hours of incubation after intradermal challenge with LTB$_4$ was selected as the routine timing for the study.

Duration studies conducted evidenced the production of measurable, reproducible wheals at the 2 hour endpoint.

In view of the results obtained when compounds of the present invention are subjected to this test, it can be demonstrated that valuable properties as $LTB_4$ antagonists are indicated.

A further test which may be used to determine the ability of compounds of this invention to exhibit $LTB_4$ antagonist activities is as follows:

Guinea Pig Polymorphonuclear Leukocyte Aggregation Assay
Isolation of guinea pig PMNs 6 ml of 6% Na-caseinate (in saline) is injected intraperitoneally into 2 male guinea pigs (250–300 g) lightly anesthetized with $CO_2$ or ether. The following day (18–24 hours post injection) the animals are sacrificed by decapitation or $CO_2$ overdose according to the SOP for nonclinical laboratory study methods.

A midline section of abdominal skin is removed and 13 ml Hanks buffer (containing 500 µl 10 mM EDTA/500 ml Hanks) plus 2 ml 7% Na-citrate is injected into the peritoneal cavity. The guinea pig is rocked back and forth 5 times. A small incision is made on the left side of the midline of the abdominal wall (avoid cutting obvious blood vessels). Use a fire-polished pasteur pipette to transfer the buffer plus cells from the abdominal cavity to 2 washed Nalgene (Oak Ridge) centrifuge tubes (half of buffer and cells in each tube). The tubes are then filled to 50 ml with additional citrate-Hanks buffer and centrifuged at 4000 rpm for 10 minutes.

Each pellet is resuspended in 1 ml of citrate-Hanks and then diluted to 50 ml with the same buffer. The cells are incubated for 30 minutes at room temperature on a Hema-Tek aliquot mixer. The cells are filtered through 2 layers of gauze into 50 ml with plastic beakers to remove PMN aggregates and then transferred to fresh, washed, 50 ml Nalgene centrifuge tubes.

The cells are centrifuged for 5 minutes, resuspended in 50 ml of fresh buffer, centrifuged again and then resuspended in 3 ml of citrate-free Hanks buffer. (Following any centrifugation the cells are always resuspended first in 1 ml of the desired fresh buffer.)

An aliquot of the washed cells, diluted 50-fold, is counted using a microscope and a hemacytometer.

The PMNs are counted as follows:

1. Dilute 50 µl of cells into 450 µl of Hank's buffer.

2. Dilute 50 µl of (1) with 150 µl of Hank's buffer plus 50 µl of Toluidine blue (50× total dilution). Add 10 µl of (2) to the hemacytometer and count cells in 16 large squares (volume counted =1 µl). View the hemacytometer under 40× magnification. The unstained cells are PMNs. Calculation: Assume 149 cells are counted.

$$\frac{\text{\# of cells counted/ml} \times \text{dilution factor} \times 2 \text{ ml}}{\text{desired final cell concentration}} = \text{buffer needed/ml of cells}$$

cell/ml = 149/.0001 = 1,490,000 cells/ml $$\frac{1.49 \times 10^6 \times 50 \times 1}{3 \times 10^7} = \frac{7.45 \times 10^8}{3 \times 10^7} = \frac{2.48 \text{ ml/ml of}}{\text{cells counted}}$$

Thus, cells must be diluted 2.48-fold with Hanks buffer (2.48×3=7.44 ml; 7.44 −3.0=4.44; add 4.44 ml buffer to the 3 ml of washed cells). This results in 7.44 ml of cells at a concentration of $3\times10^7$ cells per ml.

Instrument adjustments

Place cuvettes containing $1\times10^7$ cells/ml (166 µl PMNs plus 334 µl buffer) plus flea magnets in the aggregometer sample wells. Turn on the Chart Advance to 30 cm/hr. Turn the attenuation dials to mid range and decrease the recorder mV range settings to 50 mV full scale. Press the red "zero" button on the aggregometer and note exactly the position of the recorder pens. Turn the aggregometer left hand "PPP" dials for each cuvette position to the left or right so that the associated recorder pens move to the exact positions noted by pressing the red "zero" button. The electrical circuits are now "balanced". Except for small balance adjustments, do not make any further changes in pen positions by adjusting the "PPP" dials.

Withdraw one of the cuvettes from the aggregometer and note the (positive) direction of recorder pen motion. Replace the cuvette. Using the recorder zero knob, move the recorder pen in the positive direction to the chart paper 95% line. The pens now should not move when the red "zero" button is pressed. The pen also should not move when the mV sensitivity range is changed to 20 or 10 mV full scale (leave at 10 mV).

PMN aggregation should cause the pen to move in the "negative" direction across the chart paper. Make comparable adjustments for the second aggregometer channel but zero the recorder pen on the opposite side of the chart paper. Finally, pressing the zero button on either the recorder or the aggregometer should not cause the pens to move more than a mm or two. This instrument configuration will result in maximal pen deflection following aggregation of cells.

Aggregation studies

To a cuvette containing 334 µl of buffer and a flea magnet, add 166 µl of PMNs, 10 µl of $Ca^{++}/Mg^{++}$(70/et mM; 1.4/0.7 mM final) and 5 µl of 10 µM cytochalasin-β allow to warm up in the aggregometer (37° C.) for 5 minutes and then add 1 µl of test compound in DMSO or DMSO carrier alone. Note compound effects, if any, for 2 minutes, then add 5 µl of the challenge agonist ($LTB_4$, PAF, etc.) and observe the response for at least 2 minutes. The standard concentrations of agonists used in this assay are arachidonic acid, 6 µM; $LTB_4$, 0.3 nM; PAF, 30 pM; and FMLP, 0.6 nM.

Aggregation is quantitated by measuring, in millimeters, the average maximum deflection of the pen line at 1 minute or less after the addition of $LTB_4$. The maximum response to a control challenge with arachidonic acid may develop somewhat more slowly than this.

Each aggregometer-recorder channel should include its own series of control aggregations. All compounds should be tested at least twice at each concentration of interest. The inhibitory activity observed is expressed as the mean percent change (inhibition) observed relative to the controls determined in that channel. Controls must include appropriate solvent blanks.

The results of the above test demonstrate that compounds within the scope of this invention inhibit the activity of $LTB_4$.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carder. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxy-propylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carder can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration.

The compounds of the present invention may be prepared by the following representative examples:

Example 1

N-methyl-N-phenethyl-2-bromoacetamide

To a solution of 27.07 g (171.95 mmol) of bromoacetyl chloride in 100 ml of methylene chloride, cooled to −25° C. by means of an external cooling bath, is added dropwise a solution of 46.5 g (343.9 mmol) of N-methyl-N-phenethyl amine in 50 ml of methylene chloride over a period of 1½ hours. The reaction mixture is stirred at −25° C. for additional 15 minutes and then allowed to equilibrate to room temperature. The reaction mixture is then partitioned between methylene chloride and water. The organic layer is washed with 1N aqueous HCl solution and water, dried over magnesium sulfate and concentrated in vacuo to give N-methyl-N-phenethyl-2-bromoacetamide which is used directly in the next step.

Example 2

5-[2-(N-methyl-N-phenethyl)amino-2-oxo]ethoxyindole

A mixture of 1 g (7.29 mmol) of 5-hydroxyindole, 2.42 g (9.4 mmol) of N-methyl-N-phenethyl-2-bromoacetamide and 1.06 g of finely ground anhydrous potassium carbonate in 20 ml of 2-butanone is heated to a gentle reflux for 18 hours. After cooling to room temperature, the solid substance is filtered off and the filtrate concentrated in vacuo to give 3 g of the crude product. Purification by dry column chromatography over silica gel eluting with a solvent system of ethyl acetate/hexane (1:1, v/v) gives 5-[2-(N-methyl-N-phenethyl)-amino- 2-oxo]ethoxyindole. NMR confirms this structure.

Example 3

5-benzyloxyindole

5-(4-methylbenzyloxy)indole

When N-methyl-N-phenethyl-2-bromoacetate is replaced in the procedure of Example 2 with α-bromotoluene or α-bromo-p-xylene then the products prepared are 5-benzyloxyindole or 5-(4-methylbenzyloxy)indole. NMR confirms these structures.

Example 4

6-benzyloxyindole

6-(4-methylbenzyloxy)indole

When 5-hydroxyindole is replaced in the procedure of Example 3 with 6-hydroxyindole then the products prepared are 6-benzyloxyindole and 6-(4-methylbenzyloxy)indole. NMR confirms these structures.

Example 5

6-[2-(N-methyl-N-phenethyl)amino-2-oxolethoxyindole

When 5-hydroxyindole is replaced in the procedure of Example 2 with 6-hydroxyindole then the product prepared is 6-[2-(N-methyl-N-phenethyl)-amino- 2-oxo]ethoxyindole.

Example 6

5-[2-(N-methyl-N-phenethyl)amino-2-oxo]ethoxyindole-3-carboxaldehyde

To 2.4 ml of N,N-dimethylformamide, stirred under nitrogen in a cooling bath of 10°–20° C. is added dropwise 0.76 ml of phosphorous oxychloride. The mixture is stirred for an additional 10 minutes and a solution of 2.2 g of N-methyl-N-phenethyl-2-(5-indolyloxy)acetamide in 6.5 ml of N,N-dimethylformamide is added dropwise. The reaction mixture is stirred at room temperature for 50 minutes and poured into 45 ml of an ice-water mixture with stirring. The mixture is adjusted to pH 7 with aqueous sodium hydroxide solution, heated in a water bath of 95° C. for three minutes and allowed to cool to room temperature. Ethyl acetate is added and the layers separated. The organic layer is washed with a small amount of 1N aqueous HCl solution and several times with brine, dried over magnesium sulfate and concentrated in vacuo. The residue is purified by dry column chromatography over silica gel eluting with a solvent system of 10% ethyl acetate in hexane to afford 5-[ 2-(N-methyl-N-phenethyl)amino- 2-oxo]ethoxyindole-3-carboxaldehyde as a beige solid substance. NMR confirms this structure.

Example 7

5-benzyloxyindole-3-carboxaldehyde

5-(4-methylbenzyloxylindole-3-carboxaldehyde

When N-methyl-N-phenethyl-2-(5-indolyloxy)acetamide is replaced in the procedure of Example 6 with 5-benzyloxyindole and 5-(4-methylbenzyloxy)indole then the products obtained are 5-benzyloxyindole-3-carboxaldehyde and 5-(4-methylbenzyloxy)indole-3-carboxaldehyde. NMR confirms these structures.

Example 8

6-benzyloxyindole-3-carboxaldehyde

6-(4-methylbenzyloxy)indole-3-carboxaldehyde

When N-methyl-N-phenethyl-2-(5-indolyloxy)acetamide is replaced in the procedure of Example 6 with 6-benzyloxyindole and 6-(4-methyl benzyloxy)indole then the products obtained are 6-benzyloxyindole-3-carboxaldehyde and 6-(4-methylbenzyloxy)indole-3-carboxaldehyde.

Example 9

6-2-N-methyl-N-phenethyl)amino-2-oxo]ethoxyindole-3-carboxaldehyde

When N-methyl-N-phenethyl-2-(5-indolyloxy)acetamide is replaced in the procedure of Example 6 with N-methyl-N-phenethyl-2-(6-indolyloxy)acetamide then the product prepared is 6-[2-(N-methyl-N-phenethyl)amino-2-oxo]ethoxyindole-3-carboxaldehyde.

Example 10

N-methyl-N-phenethyl-2-(5-benzyloxy-3-formyl)indol-1-yl]acetamide

To a suspension of sodium hydride (615 mg, 80% dispersion in mineral oil, 20.5 mmol) in 90 ml of tetrahydrofuran, cooled to 0° C. by means of an external ice bath, is added in portions 4.9 g (19.52 mmol) of 5-benzyl-oxyindole- 3-carboxaldehyde. The reaction mixture is stirred in the ice bath for an additional 10 minutes and 5 g (19.52 mmol) of N-methyl-N-phenethyl-2-bromoacetamide added. The resulting mixture is stirred at room temperature for 18 hours.

The reaction mixture is filtered through Cellite® to remove the precipitate and the filtrate concentrated in vacuo to give an oily substance. Purification of this crude product by chromatography over silica gel eluting with a solvent system of methylene chloride/ethyl acetate (2:1, v/v) gives N-methyl-N-phenethyl- 2-[(5-benzyloxy-3-formyl)indol-1-yl]acetamide as a white powder (m.p. 78°–80° C.).

Example 11

N-methyl-N-phenethyl-2-(6-benzyloxy-3-formyl)indol-1-yl]acetamide

When 5-benzyloxyindole-3-carboxaldehyde in the procedure of Example 10 is replaced by 6-benzyloxyindole-3-carboxaldehyde then the compound prepared is N-methyl-N-phenethyl-2-[(6-benzyloxy-3-formyl)indol-1-yl]acetamide. NMR confirms structure.

Example 12

N-methyl-N-phenethyl-2-[(5(2-methylphenethylamino-2-oxo)ethoxy-3-formyl)indol-1-yl]acetamide When 5-benzyloxyindole-3-carboxaldehyde in the procedure of Example 10 is replaced by 5-[2-(N-methyl-N-phenethyl)amino-2-oxo]-ethoxyindole- 3-carboxaldehyde then the product prepared is N-methyl-N-phenethyl- 2-[(5-(2-methylphenethylamino-2-oxo)ethoxy-3-formyl)indol-1-yl]acetamide.

Example 13

N-methyl,
N-phenethyl-2-[(6-(2-methylphenethylamino-2-oxo)
ethoxy-3-formyl)indol-1-yl]acetamide When 5-benzyloxyindole-3-carboxaldehyde in the procedure of Example 10 is replaced by 6-[2-(N-methyl-N-phenethyl)amino-2-oxo]-ethoxyindole- 3-carboxaldehyde then the product prepared is N-methyl-N-phenethyl- 2-[(6-(2-methylphenethylamino-2-oxo)ethoxy-3-formyl)indol-1-yl] acetamide.

Example 14

N-methyl-N-(4-methoxy)phenethyl-2-bromoacetamide

A mixture of 0.55 g of N-methyl-N-(4-methoxy)-phenethylamine, 0.51 g of bromoacetic acid and 1.56 g of 1-cyclohexyl-3-(2-morpholinoethyl)carbodiimide metho-p-toluenesulfonate in 10 ml of methylene chloride is stirred at room temperature for 48 hours. The reaction mixture is filtered and the filtrate is concentrated in vacuo to give an oily residue. Purification of the residue by dry column chromatography over silica gel eluting with a solvent system of hexane/ethyl acetate (2:1, v/v) gives 0.884 g of N-methyl-N-(4-methoxy)phenethyl- 2-bromoacetamide as a beige oil. NMR confirms this structure.

Example 15

N-(4-methoxy)phenethyl-N-methyl-2-[(5-benzyloxy-3-formyl)indol-1-yl]acetamide

When N-methyl-N-phenethyl-2-bromoacetamide in the procedure of Example 10 is replaced by N-methyl-N-(4-methoxy)phenethyl-2-bromoacetate then the product prepared is N-(4-methoxy)phenethyl-N-methyl-2-[(5-benzyloxy- 3-formyl)indol-1-yl]acetamide. NMR confirms this structure.

Example 16

2-methyl-4-benzyloxyindole 7-benzyloxyindole

When 5-hydroxyindole in the procedure of Example 3 is replaced with 2-methyl- 4-hydroxyindole or 7-hydroxyindole then the products prepared are 2-methyl- 4-benzyloxyindole and 7-benzyloxyindole.

Example 17

2-methyl-4-benzyloxyindole-3-carboxaldehyde 7-benzyloxyindole-3-carboxaldehyde

When 5-benzyloxyindole in the procedure of Example 7 is replaced by 2-methyl-4-benzyloxyindole and 7-benzyloxy-indole then the products prepared are 2-methyl-4-benzyl-oxyindole-3-carboxaldehyde and 7-benzyloxyindole-3-carboxaldehyde.

Example 18

N-methyl-N-phenethyl-2-[(4-benzyloxy-3-formyl)
indol-1-yl]acetamide

When 5-benzyloxyindole-3-carboxaldehyde in the procedure of Example 10 is replaced by 4-benzyloxyindole-3-carboxaldehyde then the product prepared is N-methyl-N-phenethyl-2-[(4-benzyloxy-3-formyl)indol-1-yl]acetamide.

Example 19

N-methyl-N-phenethyl-2-[(7-benzyloxy-3-formyl)
indol-1-yl]acetamide

When 5-benzyloxyindole-3-carboxaldehyde in the procedure of Example 10 is replaced by 7-benzyloxyindole-3-carboxaldehyde then the product prepared is N-methyl-N-phenethyl-2-[(7-benzyloxy-3-formyl)indol-1-yl]acetamide. NMR confirms this structure.

Example 20

N-methyl-N-phenethyl-2-[(5-(4-methylbenzyloxyl)-3-formyl)indol-1-yl]acetamide

When 5-benzyloxyindole-3-carboxaldehyde in the procedure of Example 10 is replaced by 5-(4-methyl-benzyloxy-)indole-3-carboxaldehyde then the product prepared is N-methyl-N-phenethyl-2-[(5-(4-methylbenzyloxy)-3-formyl)indol-1-yl]acetamide. NMR confirms this structure.

Example 21

1-benzyl-5-[2-(N-methyl-N-phenethyl)amino-2-oxo]
ethoxyindole-3-carboxaldehyde

When N-methyl-N-phenethyl-2-bromoacetamide in the procedure of Example 12 is replaced by benzyl bromide then the compound prepared is 1-benzyl-5-[2-(N-methyl-N-phenethyl)amino-2-oxo]ethoxyindole-3-carboxaldehyde. NMR confirms this structure.

Example 22

N-methyl-N-phenethyl-2-[5-benzyloxy-3-(2-carbethoxyvinyl)indol-1-yl]acetamide

To a suspension of NaH (1.68 g, 80% dispersion in mineral oil, 56 mmol) in 150 ml of tetrahydrofuran, stirred in an ice bath under an atmosphere of nitrogen, is added dropwise a solution of 11.25 ml (98% reagent, 54.45 mmol) of triethyl phosphonoacetate in 30 ml of THF. The resulting mixture is stirred in the ice bath for an additional 20 minutes and a solution of N-methyl-N-phenethyl- 2-[(5-benzyloxy-3-formyl)indol-1-yl]acetamide (15.5 g, 36.3 mmol)in 80 ml of THF is added quickly. The ice bath is then removed and the mixture stirred for 18 hours at room temperature.

The reaction is quenched with water and ethyl acetate is added. The layers are separated and the organic layer is washed with brine, dried over MgSO$_4$ and concentrated in vacuo to give a beige oil. The crude product is purified by dry column chromatography over silica gel eluting with a solvent system of 10% ethyl acetate in methylene chloride to give N-methyl-N-phenethyl- 2-[5-benzyloxy-3-(2-carbethoxyvinyl)indol-1-yl]acetamide. Trituration of this substance in diethyl ether gives pure compound as a white powder (m.p. 136°–139° C. (dec)).

Example 23

N-methyl-N-phenethyl-2[-5-benzyloxy-3-(2-carboxyvinyl)indol-1-yl]acetamide

To a suspension of 14.85 g (29.9 mmol) of N-methyl-N-phenethyl-2-[5-benzyloxy- 3-(2-carbethoxyvinyl)indol-1-yl]acetamide in 750 ml of ethanol is added a solution of 2.52 g of potassium hydroxide in 40 ml of water. The resulting suspension is stirred in a heating bath of 50° C. for 20 hours and another batch of KOH solution (1.75 g of KOH in 40 ml of water) is added. The mixture is stirred at 50° C. for seven days after which time a homogeneous solution is obtained.

After cooling to room temperature, ethanol is removed in vacuo. The residue is mixed with water and the unreacted ester extracted into ethyl acetate. The pH of the aqueous layer is adjusted to about 7 with 1N aqueous HCl solution. The white precipitate obtained is collected by filtration, washed with water and dried in vacuo to yield N-methyl-N-phenethyl-2-[5-benzyloxy-3-(2-carboxyvinyl)indol-1-yl] acetamide as a white powder (m.p. 190°–192° C. (dec)).

Example 24

N-methyl-N-phenethyl-2-[5-benzyloxy-3-(2-(1-pyrrolidinecarbonyl)vinyl)indol-1-yl]acetamide

To a mixture of 0.63 g (1.34 mmol) of N-methyl-N-phenethyl-2-(5-benzyloxy- 3-(2-carboxyvinyl)indol-1-yl]-acetamide in 15 ml of methylene chloride, cooled to 0° C. with an external ice bath, is added dropwise 0.26 ml (3.02 mmol) of oxalyl chloride, followed immediately with 3 drops of N,N-dimethylformamide. The mixture is stirred in an ice bath for 30 minutes and then for 1 hour with the cooling bath removed. The reaction mixture is then concentrated in vacuo. The residue obtained is dissolved in 10 ml of methylene chloride and this solution is added dropwise to a mixture of 0.11 ml (1.34 mmol) of pyrrolidine, 0.24 ml of pyridine and 15 ml of methylene chloride with stirring at 0° C. (ice bath). The resulting reaction mixture is stirred at room temperature for several hours and quenched with saturated aqueous NH$_4$Cl solution. Ethyl acetate and water are added and the layers separated. The organic layer is washed with 1N aqueous HCl solution and water, dried over magnesium sulfate and concentrated in vacuo. The residue is triturated in hot ethyl acetate to give N-methyl-N-phenethyl-2-[5-benzyloxy-3-(2-(1-pyrrolidinecarbonyl)-vinyl)indol-1-yl]acetamide (m.p. 185°–187° C.).

Example 25

N-methyl-N-phenethyl-2[-5-benzyloxy-3-(2-carbethoxyethyl)indol-1-yl]acetamide

A mixture of 0.93 g of N-methyl-N-phenethyl-2-[5-benzyloxy-3-(2-carbethoxyvinyl)indol- 1-yl]acetamide, 0.5 g of 10% palladium on activated carbon and 150 ml of ethanol is shaken under 40 psi of hydrogen on a Parr Apparatus for 40 minutes. The mixture is filtered to remove the catalysts and the filtrate is concentrated in vacuo. The residue is purified by dry column chromatography over silica gel eluting with a solvent system of ethyl acetate/hexane (2:1, v/v) to give N-methyl-N-phenethyl-2-[5-benzyloxy-3-(2-carbethoxyethyl)indol- 1-yl]acetamide as white powder (m.p. 81°–83° C.).

Example 26

N-methyl-N-phenethyl-2-[5-benzyloxy-3-(2-carboxyethyl)indol-1-yl]acetamide

To a suspension of 0.7 g (1.4 mmol) of N-methyl-N-phenethyl-2-[5-benzyloxy- 3-(2-carbethoxyethyl)indol-1-yl]acetamide in 20 ml of ethanol is added a solution of 0.2 g of potassium hydroxide in 3 ml of water. The mixture is stirred at room temperature for 18 hours and concentrated in vacuo. The residue is dissolved in water and the resulting solution adjusted to pH 4 with 1N aqueous HCl solution. The precipitate which forms is extracted into ethyl acetate. The organic solution is washed with brine, dried over magnesium sulfate and concentrated in vacuo to give N-methyl-N-phenethyl-2-[5-benzyloxy- 3-(2-carboxyethyl)indol-1-yl]acetamide as a beige powder (m.p. 122°–125° C.).

Example 27

N-(4-methoxyphenethyl)-N-methyl-2-[(5-benzyloxy-3-(2-carbethoxyvinyl)indol-1-yl]acetamide

When N-methyl-N-phenethyl-2-[(5-benzyloxy-3-formyl)-indol-1-yl]acetamide in the procedure of Example 22 is replaced with N-(4-methoxy)phenethyl-N-methyl-2-[(5-benzyloxy-3-formyl)indol-1-yl]acetamide then the product prepared is N-(4-methoxyphenethyl)-N-methyl-2-[(5-benzyloxy- 3-(2-carbethoxyvinyl)indol-1-yl]acetamide. NMR confirms this structure.

Example 28

N-methyl-N-phenethyl-2-6-benzyloxy-3-(2-carbethoxyvinyl)indol-1-yl]acetamide

When N-methyl-N-phenethyl-2-[(5-benzyloxy-3-formyl)-indol-1-yl)]acetamide in the procedure of Example 22 is replaced with N-methyl-N -phenethyl-2-[(6-benzyloxy-3-formyl)indol-1-yl]acetamide then the product prepared is N-methyl-N-phenethyl-2-[6-benzyloxy-3-(2-carbethoxyvinyl)-indol-1-yl]acetamide. NMR confirms this structure.

Example 29

N-methyl-N-phenethyl-2-[4-benzyloxy-3-(2-carbethoxyvinyl indol-1-yl]acetamide

When N-methyl-N-phenethyl-2-[(5-benzyloxy-3-formyl)-indol-1-yl]acetamide in the procedure of Example 22 is replaced with N-methyl-N-phenethyl- 2-[(4-benzyloxy-3-formyl)indol-1-yl]acetamide then the product prepared is N-methyl-N-phenethyl-2-[4-benzyloxy-3-(2-carbethoxyvinyl)-indol-1-yl]acetamide. (m.p. 110°–120° C.)

Example 30

N-methyl-N-phenethyl-2-[7-benzyloxy-3-(2-carbethoxyvinyl indol-1-yl]acetamide

When N-methyl-N-phenethyl-2-[(5-benzyloxy-3-formyl)indol-1-yl]acetamide in the procedure of Example 22 is replaced with N-methyl-N-phenethyl- 2-[(7-benzyloxy-3-formyl)indol-1-yl]acetamide then the product prepared is N-methyl-N-phenethyl-2-[7-benzyloxy-3-(2-carbethoxyvinyl)indol-1-yl]acetamide. NMR confirms this structure.

Example 31

N-methyl-N-phenethyl-2-[3-(2-carbethoxyvinyl)-5-(2-(N-methyl-N-phenethyl)amino-2-oxo)ethoxyindole-1-yl]acetamide When N-methyl-N-phenethyl-2-[(5-benzyloxy-3-formyl)indol-1-yl]acetamide in the procedure of Example 22 is replaced with N-methyl-N-phenethyl- 2-[(5-(2-methylphenethylamino-2-oxo)ethoxy-3-formyl)indol-1 -yl]acetamide then the product prepared is N-methyl-N-phenethyl-2-[3-(2-carbethoxyvinyl)- 5-(2-(N-methyl-N-phenethyl)amino-2-oxo)ethoxyindol-1-yl]acetamide. NMR confirms this structure.

Example 32

N-methyl-N-phenethyl-2-3-(2-carbethoxyvinyl)-5-(4-methylbenzyloxyl)indol-1-yl]acetamide When N-methyl-N-phenethyl-2-[(5-benzyloxy-3-formyl)indol-1-yl]acetamide in the procedure of Example 22 is replaced with N-methyl-N-phenethyl- 2-[(5-(4-methylbenzyloxy)-3-formyl)indol-1-yl]acetamide then the product prepared is N-methyl-N-phenethyl-2-[3-(2-carbethoxyvinyl)-5-( 4-methylbenzyloxy)indol-1-yl]acetamide. NMR confirms this structure.

Example 33

1-benzyl-3-(2-carbethoxyvinyl)-5-[2-(N-methyl-N-phenethyl)amino- 2-oxo]ethoxyindole When N-methyl-N-phenethyl-2-[(5-benzyloxy-3-formyl)indol-1-yl]acetamide in the procedure of Example 22 is replaced with 1-benzyl-5-[2-(N-methyl-N-phenethyl)amino- 2-oxo]ethoxyindole-3-carboxaldehyde then the product prepared is 1-benzyl-3-(2-carbethoxyvinyl)-5-[2-(N-methyl-N-phenethyl)amino- 2-oxo]ethoxyindole. NMR confirms this structure.

Example 34

When triethylphosphonoacetate in the procedure of Example 22 is replaced with the phosphonates of Table I below and N-methyl-N-phenethyl-2-[(5-benzyloxy-3-formyl)indol-1-yl]acetamide is replaced by the various aldehydes and ketones of this invention then the corresponding product is prepared. A representative list of compounds so prepared may be found in Examples 35–41 of Table II below.

TABLE I trimethylphosphonoacetate
triethylphosphonoacetate
tripropylposphonoacetate
tributylphosphonoacetate
tri-tert-butylphosphonoacetate
triethylphosphono-2-propionate
triethylphosphono-3-butanoate
triethylphosphono-2-buten-2-oate
triethylphosphono-4-buten-2-oate

TABLE II

Example 35

N-methyl-N-phenethyl-2[-5-benzyloxy-3-(2-carb-t-butoxyvinyl)indol- 1-yl]acetamide (Solvent system ethylacetate/hexane; m.p. 135° C. (dec.).)

Example 36

N-methyl-N-phenethyl-2-[5-benzyloxy-3-(2-carbmethoxyvinyl)indol-1-yl]acetamide

NMR confirms this structure. (m.p. 155°–156° C.)

Example 37

N-methyl-N-phenethyl-2-[2-methyl-4-benzyloxy-3-(2-carbethoxy-2-methylvinyl)indol-1-yl]acetamide

Example 38

N-methyl-N-phenethyl-2-[5-benzyloxy-3-(2-carbethoxy-2-ethylvinyl)indol-1-yl]acetamide (m.p. 130°–131° C. (dec.))

Example 39

N-methyl-N-phenethyl-2-[1-benzyloxy-3-(2-carbethoxy-2-methylvinyl)indol-5-yl]acetamide

Example 40

N-methyl-N-phenethyl-2-[4-benzyloxy-3-(4-carbethoxy-2-ethylvinyl)indol-1-yl]acetamide

Example 41

N-methyl-N-phenethyl-2-[5-benzyloxy-3-(2-carbethoxy-1,3-butadienyl)indol-1-yl]acetamide NMR confirms this structure.

Example 42

N-(4-methoxyphenethyl)-N-methyl-2 [-(5-benzyloxy-3-(2-carboxyvinyl)indol-1-yl]acetamide When N-methyl-N-phenethyl-2-[5-benzyloxy-3-(2-carboethoxy-vinyl)indol- 1-yl]acetamide in the procedure of Example 23 is replaced with N-(4-methoxyphenethyl)-N-methyl-2-[(5-benzyloxy-3-(2-carbethoxyvinyl)indol-1-yl] acetamide then the product prepared is N-(4-methoxyphenethyl)-N-methyl- 2-[(5-benzyloxy-3-(2-carboxyvinyl)indol-1-yl]acetamide. (m.p. 161°–162° C. (dec.))

Example 43

N-methyl-N-phenethyl-2-[6-benzyloxy-3-(2-carboxyvinyl)indol-1-yl]acetamide

When N-methyl-N-phenethyl-2-[5-benzyloxy-3-(2-carboethoxy-vinyl)indol- 1-yl]acetamide in the procedure of Example 23 is replaced with N-methyl-N-phenethyl-2-[6-benzyloxy-3-(2-carbethoxyvinyl)indol-1-yl]acetamide then the product prepared is N-methyl-N-phenethyl-2-[6-benzyloxy-3-(2-carboxyvinyl)indol-1-yl]acetamide. (m.p. 201°–202° C. (dec.))

Example 44

N-methyl-N-phenethyl-2-[4-benzyloxy-3-(2-carboxyvinyl)indol-1-yl]acetamide

When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[4-benzyloxy-3-(2-carbethoxyvinyl)indol-1-yl]acetamide then the product prepared is N-methyl-N-phenethyl-2-[4-benzyloxy-3-(2-carboxyvinyl)-indol- 1-yl]acetamide. (m.p. 173°–175° C. (dec.))

Example 45

N-methyl-N-phenethyl-2-[7-benzyloxy-3-(2-carboxyvinyl)indol-1-yl]acetamide

When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[7-benzyloxy-3-(2-carbethoxyvinyl)indol-1-yl]acetamide then the product prepared is N-methyl-N-phenethyl-2-[7-benzyloxy-3-(2-carboxyvinyl)-indol- 1-yl]acetamide. (m.p. 192°–193° C. (dec.))

Example 46

N-methyl-N-phenethyl-2-[3-(2-carboxyvinyl)-5-(2-(N-methyl-N-phenethyl)amino-2-oxo)ethoxyindol-1-yl]acetamide When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[3-(2-carbethoxyvinyl)-5-(2-(N-methyl-N-phenethyl)amino-2-oxo)ethoxyindol-1 -yl]acetamide then the product prepared is N-methyl-N-phenethyl- 2-[3-(2-carboxyvinyl)-5-(2-(N-methyl-N-phenethyl)amino-2-oxo)-ethoxyindol- 1-yl]acetamide. (m.p. 94°–96° C. (dec.))

Example 47

N-methyl-N-phenethyl-2-[3-(2-carboxyvinyl)-5-(4-methylbenzyloxy)indol-1-yl]acetamide When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[3-(2-carbethoxyvinyl)-5-(4-methylbenzyloxy)indol-1-yl]acetamide then the product prepared is N-methyl-N-phenethyl-2-[3-(2-carboxyvinyl)- 5-(4-methylbenzyloxy)indol-1-yl]acetamide. (m.p. 164°–166° C.)

Example 48

N-methyl-N-phenethyl-2-[5-benzyloxy-3-(2-carboxy-2-methylvinyl)indol-1-yl]acetamide N-methyl-N-phenethyl-2-[5-benzyloxy-3-(2(Z)-carboxy-2-methylvinyl)indol-1-yl]acetamide When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[5-benzyloxy-3-(2-carbethoxy-2-methylvinyl)indol-1-yl]acetamide then the product prepared is N-methyl-N-phenethyl-2-[5-benzyloxy-3-(2-carboxy-2-methylvinyl)-5-(4-methoxybenzyloxy)indol-1-yl]acetamide. (m.p. 220°–231° C. (dec.))

When N-methyl-N-phenethyl-2-[5-benzyloxy-3-(2-carbethoxyvinyl)indol-1-yl]acetamide in the procedure of Example 23 is replaced with N-methyl-N-phenethyl- 2-[5-benzyloxy-3-(2-(Z)-carbethoxyvinyl)indol-1-yl]acetamide, then the product prepared is N-metyl-N-phenethyl-2-[5-benzyloxy-3-(Z)-2-carboxy-2-methylvinyl)indol-1-yl]acetamide as a white powder. (m.p. 155°–160° C.)

Example 49

N-methyl-N-phenethyl-2-[5-benzyloxy-3-(4-carboxy-1,3-butadienyl)indol-1-yl]acetamide When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[1-benzyloxy-3-(2-carbethoxy-2-methylvinyl)indol-5-yl]acetamide then the product prepared is N-methyl-N-phenethyl-2-[5-benzyloxy-3-(2-carboxy-1,3-butadienyl)indol-1-yl] acetamide. (solvent system (acetone/ether) m.p. 189°–190° C.)

Example 50

1-benzyl-3-(2-carboxyvinyl)-5-[2-(N-methyl-N-phenethyl)amino- 2-oxo]ethoxyindole When N-methyl-N-phenethyl-2-[5-benzyloxy-3-(2-carboethoxyvinyl)-indol- 1-yl]acetamide in the procedure of Example 23 is replaced with 1-benzyl-3-(2-carbethoxyvinyl)-5-[2-(N-methyl-N-phenethyl)amino-2-oxo]ethoxyindole then the product prepared is 1-benzyl-3-(2-carboxyvinyl)-5-[2-(N-methyl-N-phenethyl)amino- 2-oxo]ethoxyindole. (m.p. 96°–99° C.)

Example 51

N-methyl-N-phenethyl-2-[2-methyl-4-benzyloxy-3-(2-carboxy-2-methylvinyl)indol-1-yl]acetamide When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[2-methyl-4-benzyloxy-3-(2-carbethoxy-2-methylvinyl)indol-1-yl]acetamide then the product prepared is N-methyl-N-phenethyl-2-[2-methyl-4-benzyloxy- 3-(2-carboxy-2-methylvinyl)indol-1-yl]acetamide.

Example 52

N-methyl-N-phenethyl-2-[5-benzyloxy-3-(2-carboxy-2-ethylvinyl)indol-1-yl]acetamide When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[5-benzyloxy-3-(2-carbethoxy-2-ethylvinyl)indol-1-yl]acetamide then the product prepared is N-methyl-N-phenethyl-2-[5-benzyloxy-3-(2-carboxy- 2-ethylvinyl)indol-1-yl]acetamide. (m.p. 205°–207° C.)

Example 53

When N-methyl-N-phenethyl-2-[5-benzyloxy-3-(2-carbethoxyvinyl)indol1-yl]acetamide in the procedure of Example 25 is replaced by the unsaturated esters of Examples 27–33 and 35–41 then the products prepared are shown in Table III below.

TABLE III

N-(4-methoxyphenethyl)-N-methyl-2-[(5-benzyloxy-3-(2-carbethoxyethyl)indol1-yl]acetamide N-methyl-N-phenethyl-2-[6-benzyloxy-3-(2-carbethoxyethyl)indol-1-yl]acetamide N-methyl-N-phenethyl-2-[4-benzyloxy-3-(2-carbethoxyethyl)indol-1-yl]acetamide N-methyl-N-phenethyl-2-[7-benzyloxy-3-(2-carbethoxyethyl)indol-1-yl]acetamide N-methyl-N-phenethyl-2-[3-(2-carbethoxyethyl)-5-(2-(N-methyl-N-phenethyl)amino-2-oxo)ethoxyindol-1-yl]acetamide N-methyl-N-phenethyl-2-[3-(2-carbethoxyethyl)-5-(4-methylbenzyloxy)indol-1-yl]acetamide 1-benzyl-3-(2-carbethoxyethyl)-5-[2-(N-methyl-N-phenethyl)amino-2-oxo]ethoxyindole N-methyl-N-phenethyl-2-[5-benzyloxy-3-(2-carb-t-butoxyethyl)indol-1-yl]acetamide N-methyl-N-phenethyl-2-[5-benzyloxy-3-(2-carbmethoxyethyl)indol-1-yl]acetamide N-methyl-N-phenethyl-2-[2-methyl-4-benzyloxy-3-(2-carbethoxypropyl)indol-1-yl]acetamide N-methyl-N-phenethyl-2-[5-benzyloxy-3-(2-carbethoxybutyl)indol-1-yl]acetamide N-methyl-N-phenethyl-2-[1-benzyl-3-(2-carbethoxypropyl)indol-5-yl]acetamide N-methyl-N-phenethyl-2-[5-benzyloxy-3-(2-carbethoxypropyl)indol-1-yl]acetamide N-methyl-N-phenethyl-2-[5-benzyloxy-3-(4-carbethoxybutyl)indol-1-yl]acetamide

Example 54

When N-methyl-N-phenethyl-2-[5-benzyloxy-3-(2-carbethoxyethyl)indol-1-yl]acetamide in the procedure of Example 26 is replaced by the compound of Table III then the products prepared are shown in Table IV below.

TABLE IV

N-(4-methoxyphenethyl)-N-methyl-2-[(5-benzyloxy-3-(2-carboxyethyl)indol-1-yl]acetamide N-methyl-N-phenethyl-2-[6-benzyloxy-3-(2-carboxyethyl)indol-1-yl]acetamide N-methyl-N-phenethyl-2-[4-benzyloxy-3-(2-carboxyethyl)indol-1-yl]acetamide N-methyl-N-phenethyl-2-[7-benzyloxy-3-(2-carboxyethyl)indol-1-yl]acetamide N-methyl-N-phenethyl-2-[3-(2-carboxyethyl)-5-(2-(N-methyl-N-phenethyl)amino-2-oxo)ethoxyindol-1-yl]acetamide N-methyl-N-phenethyl-2-[3-(2-carboxyethyl)-5-(4-methylbenzyloxy)indol-1-yl]acetamide 1-benzyl-3-(2-carboxyethyl)-5-[2-(N-methyl-N-phenethyl)amino-2-oxo]ethoxyindole N-methyl-N-phenethyl-2-[5-benzyloxy-3-(2-carboxyethyl)indol-1-yl]acetamide N-methyl-N-phenethyl-2-[5-benzyloxy-3-(2-carboxyethyl)indol-1-yl]acetamide N-methyl-N-phenethyl-2-[2-methyl-4-benzyloxy-3-(2-carboxypropyl)indol-1-yl]acetamide N-methyl-N-phenethyl-2-[5-benzyoxy-3-(2-carboxybutyl)indol-1-yl]acetamide N-methyl-N-phenethyl-2-[1-benzyl-3-(2-carboxypropyl)indol-5-yl]acetamide N-methyl-N-phenethyl-2-[5-benzyloxy-3-(2-carboxypropyl)indol-1-yl]acetamide N-methyl-N-phenethyl-2-[5-benzyloxy-3-(4-carboxybutyl)indol-1-yl]acetamide

Example 55

N-methyl-N-phenethyl-2-[5-benzyloxy-3-2-cyanovinyl)indol-1-yl]acetamide

To a suspension of 2 g (8.30 mmoles) of acetonitriletriphenylphosphonium bromide (prepared from 1.24 g bromo-acetonitrile and 2.98 g triphenylphosphine refluxed in toluene for 1 hour) in 100 ml of dimethylformamide is added 0.27 g (9.13 mmoles) of an 80% sodium hydride in oil dispersion. After stirring at 0° C. for 1 hour, 3.54 g (8.30 mmoles) of N-methyl-N-phenethyl- 2-[(5-benzyloxy-3-formyl)indol-1-yl]acetamide in 20 ml of dimethylformamide is added and stirred for 2 hours. The mixture is poured into ice water, extracted with ethyl acetate which is dried and concentrated in vacuo. Purification by flash column chromatography through silica gel gives N-methyl-N-phenethyl-2-[5-benzyloxy-3-(2-cyanovinyl)indol-1-yl]acetamide.

Example 56

N-methyl-N-phenethyl-2-[5-benzyloxy-3-(2-tetrazol-5-yl)vinylindol-1-yl]acetamide A suspension of 0.94 g (2 mmoles) of N-methyl-N-phenethyl-2-[5-benzyloxy- 3-(2-cyanovinyl)indol-1-yl]acetamide, 0.56 g (10.45 mmoles)of ammonium chloride and 0.68 g (10.45 mmoles) of sodium azide in 20 ml of dimethylformamide is heated at 100° C. for 18 hours. The mixture is poured into ice water. Addition of ethyl acetate gives a precipitate which is collected and triturated in acetone to give N-methyl-N-phenethyl-2-[5-benzyloxy-3-(2-tetrazol-5-yl)vinylindol-1-yl]acetamide. (m.p. 203°–205° C.)

Example 57

N-methyl-N-phenethyl-2-[5-benzyloxy-3-(2-2-tetrazol-5-yl)ethylindol-1-yl]acetamide To a solution 0.2 g (0.42 mmoles) of N-methyl-N-phenethyl-2-[5-benzyloxy- 3-(2-tetrazol-5-ylvinyl)indol-1-yl]acetamide in 30 ml of ethanol is added 0.08 g of 10% palladium on carbon and the mixture is shaken under 30 psi of hydrogen for 4 hours. The mixture is filtered and the filtrate concentrated in vacuo. The residue is crystallized from methylene chloride to give N-methyl-N-phenethyl-2-[5-benzyloxy-3-(2-tetrazol-5-yl)ethylindol-1-yl]acetamide.

Example 58

When bromoacetonitrile in the procedure of Example 55 is replaced with the reagents of Table V below then the corresponding products are prepared which are further convened to the corresponding tetrazoles by Examples 56 and 57.

TABLE V bromoacetonitrile
3-bromopropanenitrile
2-bromopropanenitrile
2-bromobutanenitrile
3-bromobutanenitrile
2-methyl-3-bromopropanenitrile
4-bromo-2-butenenitrile
4-bromo-2-pentenenitrile Example 59

When N-methyl-N-phenethyl-2-[(5-benzyloxy-3-formyl)indol-1-yl]acetamide is replaced in Example 55 and 58 with the aldehydes and ketones of this invention the corresponding tetrazoles are prepared. A representative list of products so prepared is shown in Table VI.

TABLE VI

N-(4-methoxyphenethyl)-N-methyl-2-[(5-benzyloxy-3-(2-tetrazol-5-yl)vinylindol-1-yl]acetamide
N-methyl-N-phenethyl-2-[6-benzyloxy-3-(2-tetrazol-5-yl)vinylindol-1-yl]acetamide
N-methyl-N-phenethyl-2-[4-benzyloxy-3-(2-tetrazol-5-yl)vinylindol-1-yl]acetamide
N-methyl-N-phenethyl-2-[7-benzyloxy-3-(2-tetrazol-5-yl)vinylindol-1-yl]acetamide
N-methyl-N-phenethyl-2-[3-(2-tetrazol-5-yl)vinyl-5-(2-(N-methyl-N-phenethyl)amino-2-oxo)ethoxyindol-1-yl]acetamide
N-methyl-N-phenethyl-2-[3-(2-tetrazol-5-yl)vinyl-5-(4-methylbenzyloxy)indol-1-yl]acetamide
1-benzyl-3-(2-tetrazol-5-yl)vinyl-5-[2-(N-methyl-N-phenethyl)amino-2-oxo]ethoxyindole
N-methyl-N-phenethyl-2-[5-benzyloxy-3-(2-tetrazol-5-yl)vinylindol-1-yl]acetamide
N-methyl-N-phenethyl-2-[4-benzyloxy-3-(2-tetrazol-5-yl-2-methylvinyl)indol-1-yl]acetamide
N-methyl-N-phenethyl-2-[5-benzyloxy-3-(2-tetrazol-5-yl-2-ethylvinyl)indol-1-yl]acetamide
N-methyl-N-phenethyl-2-[1-benzyl-3-(2-tetrazol-5-yl-2-methylvinyl)indol-5-yl]acetamide
N-methyl-N-phenethyl-2-[5-benzyloxy-3-(2-tetrazol-5-yl-2-methylvinyl)indol-1-yl]acetamide
N-methyl-N-phenethyl-2-[5-benzyloxy-3-(4-tetrazol-5-yl-1,3-butadienyl)indol-1-yl]acetamide
N-(4-methoxyphenethyl)-N-methyl-2-[5-benzyloxy-3-(2-tetrazol-5-ylethyl)indol-1-yl]acetamide
N-(4-methoxyphenethyl)-N-methyl-2-[4-benzyloxy-3-(2-tetrazol-5-ylethyl)indol-1-yl]acetamide
N-(4-methoxyphenethyl)-N-methyl-2-[7-benzyloxy-3-(2-tetrazol-5-ylethyl)indol-1-yl]acetamide
N-(4-methoxyphenethyl)-N-methyl-2-[5-(2-(N-methyl-N-phenethyl)amino-2oxo)-3-(2-tetrazol-5-ylvinyl)ethoxyindol-1-yl]-acetamide
N-(4-methoxyphenethyl)-N-methyl-2-[5-(4-methylbenzyloxy)-3-(2-tetrazol-5-ylvinyl)indol- 1-yl]acetamide
1-benzyl-3-(2-tetrazol-5-ylethyl)-5-[2-(N-methyl-N-phenethyl)amino-2-oxo]ethoxyindole
N-methyl-N-phenethyl-2-[5-benzyloxy-3-(2-tetrazol-5-yl)ethylindol-1-yl]acetamide
N-methyl-N-phenethyl-2-[4-benzyloxy-3-(2-tetrazol-5-ylpropyl)indol-1-yl]acetamide
N-methyl-N-phenethyl-2-[5-benzyloxy-3-(2-tetrazol-5-ylbutyl)indol-1-yl]acetamide
N-methyl-N-phenethyl-2-[1-benzyl-3-(2-tetrazol-5-ylpropyl)indol-5-yl]acetamide
N-methyl-N-phenethyl-2-[5-benzyloxy-3-(2-tetrazol-5-ylpropyl)indol-1-yl]acetamide
N-methyl-N-phenethyl-2-[5-benzyloxy-3-(4-tetrazol-5-yl)butylindol-1-yl]acetamide Example 60

N-methyl-N-phenethyl-2-[5-benzyloxy-3-(4-carboxy-3-methyl-3-butenyl)indol-1-yl]acetamide Step A: N-methyl-N-phenethyl-2[-3-(2-acetyl)vinyl-5-benzyloxyindol-1-yl]acetamide A mixture 2 g (4.68 mmol) of N-methyl-N-phenethyl-2-[3-benzyloxy-2-formylindol- 1-yl]acetamide, 125 ml of acetone and 25 ml of 1N aqueous sodium hydroxide solution is stirred at room temperature for 72 hours. The mixture is then concentrated in vacuo. The pH of the concentrated mixture is adjusted to about 6 with 1N aqueous HCl solution. Ethyl acetate is added and the layers separated. The organic layer is washed with brine, dried over magnesium sulfate and concentrated in vacuo. The yellow foamy residue is triturated in ether/acetone to give N-methyl-N-phenethyl-2-[3-(2-acetyl)vinyl-5-benzyloxyindol- 1-yl]acetamide. (m.p. 150°–152° C.)

Step B: N-methyl-N-phenethyl-2-[3-(2-acetylethyl-5-benzyloxyindol-1-yl]acetamide When the procedure of Example 25 is followed, N-methyl-N-phenethyl-2-[3-(2-acetyl)vinyl-5-benzyloxyindol-1-yl]acetamide is hydrogenated to N-methyl-N-phenethyl-2-[3-(2-acetylethyl))-5-benzyloxyindol-1-yl]acetamide. (m.p. 120–121° C.)

Step C: N-methyl-N-phenethyl-2-[5-benzyloxy-3-(4-carbethoxy-3-methyl-3-butenyl)indol-1-yl]acetamide When the procedure of Example 22 is followed, N-methyl-N-phenethyl-2-[3-acetylethyl-5-benzyloxyindol-1-yl] acetamide is reacted with triethylphosphonoacetate to give N-methyl-N-phenethyl-2-[5-benzyloxy-3-(4-carbethoxy-3-methyl-3-butenyl)indol-1-yl]acetamide as a yellow oil which is NMR verified.

Step D: N-methyl-N-phenethyl-2[-5-benzyloxy-3-(4-carboxy-3-methyl-3-butenyl)indol-1yl]acetamide When the procedure of Example 26 is followed, N-methyl-N-phenethyl-2-[5-benzyloxy-3-(4-carbethoxy-3-methyl-3-butenyl)indol-1-yl]acetamide is hydrolyzed to give N-methyl-N-phenethyl-2-[5-benzyloxy-3-(4-carboxy-3-methyl- 3-butenyl)indol-1-yl]acetamide as a yellow foamy substance. NMR confirms this structure.

Example 61

N-methyl-N-phenethyl-2-(5-benzyloxy-2-carboxyindol-1-yl)acetamide

N-methyl-N-phenethyl-2-(5-benzyloxy-3-carboxyindol-1-yl)acetamide

Step A: N-methyl-N-phenethyl-2-(5-benzyloxy-2-carbomethoxyindol-1-yl)acetamide

Following the procedure of Example 10, 5-benzyloxy-2-carbomethoxyindole is alkylated with N-methyl-N-phenethyl-2-bromoacetamide to give N-methyl-N-phenethyl-2-(5-benzyloxy-2-carbomethoxyindol-1-yl)acetamide. (m.p. 155°–156° C.)

Step B: N-methyl-N-phenethyl-2-(5-benzyloxy-2-carboxyindol-1-yl)acetamide

Following the procedure of Example 23 the ester of Step A is hydrolyzed to give N-methyl-N-phenethyl-2-(5-benzyloxy-2-carboxyindol-1-yl)acetamide. (m.p. 250° C. (dec.))

Step C: N-methyl-N-phenethyl-2-(5-benzyloxy-3-carboxyindol-1-yl)acetamide

When 5-benzyloxy-3-carbomethoxyindol is used in Step A and the alkylated product obtained is then hydrolyzed according to Step B, N-methyl-N-phenethyl- 2-(5-benzyloxy-3-carboxyindol-1-yl]acetamide is prepared. (m.p. 182°–185° C.)

Example 62

N-methyl-N-phenethyl-2-[5-benzyloxy-1-(2-carboxyvinyl)indol-3-yl]acetamide

Step A: N-methyl-N-phenethyl-2-(5-benzyloxyindol-3-yl)acetamide

When the procedure of Example 14 is followed, 5-benzyloxyindole-3-acetic acid and N-methyl-N-phenethylamine are reacted to give N-methyl-N-phenethyl- 2-(5-benzyloxyindol-3-yl)acetamide. (m.p. 146° C. (dec.))

Step B: N-methyl-N-phenethyl-2-[5-benzyloxy-1-(2-carbethoxyvinyl)indol-3-yl]acetamide To a mixture of 1.579 g (3.96 mmol) of N-methyl-N-phenethyl-2-(5-benzyloxyindol- 3-yl)acetamide and 0.4 ml of benzyltrimethylammonium hydroxide (40% solution in methanol) in 15 ml of dioxane is added with stirring 0.44 ml (0.43 g, 4.35 mmol) of ethyl propriolate. A reddish solution is obtained, which is stirred at room temperature for 18 hours and concentrated in vacuo. The residue is taken up in ethyl acetate, washed with brine, dried over magnesium sulfate and concentrated in vacuo. The residue is purified by dry column chromatography over silica gel eluting with a solvent system of 5% ethyl acetate in methylene chloride to yield 450 mg of N-methyl-N-phenethyl-2-[5-benzyloxy-1-(2-carbethoxyvinyl)indol-3-yl]acetamide.

Step C: N-methyl-N-phenethyl-2-[5-benzyloxy-1-(2-carboxyvinyl)indol-3yl]acetamide Following the procedure of Example 23 the ester of Step B is hydrolyzed to N-methyl-N-phenethyl-2-[5-benzyloxy-1-(2-carboxyvinyl)indol-3-yl]acetamide. (m.p. 104°–108° C. (dec.))

Example 63

When pyrrolidine in the procedure of Example 24 is replaced with a suitable amine and N-methyl-N-phenethyl-2-[5-benzyloxy-3-(2-carboxyvinyl)-indol- 1-yl]acetamide is replaced by the acids prepared by the above examples, then the corresponding amide is prepared.

Example 64

N-benzyl-5-benzyloxy-3-(2-tetrazol-5-ylethyl)indole

Step A: N-benzyl-5-benzyloxy-3-formylindole

Following the procedure of Example 10, benzyl bromide is used in place of N-methyl-N-phenethyl-2-bromoacetamide to give N-benzyl-5-benzyloxy-3-formylindole.

Step B: N-benzyl-5-benzyloxy-3-(2-cvanovinyl)indole

Following the procedure of Example 55, N-benzyl-5-benzyloxy-3-formylindole is treated with acetonitrile triphenylphosphonium bromide to give N-benzyl-5-benzyloxy-3-(2-cyanovinyl)indole.

Step C: N-benzyl-5-benzyloxy-3-(2tetrazol-5-ylvinyl)indole

Following the procedure of Example 56, N-benzyl-5-benzyloxy-3-(2-cyanovinyl)indole is reacted with the sodium azide to give N-benzyl-5-benzyloxy- 3-(2-tetrazol-5-ylvinyl)indole. (m.p. 178°–180° C. (dec.))

Step D: N-benzyl-5-benzyloxy-3-(2-tetrazol-5-ylethyl)indole

Following the procedure of Example 57, N-benzyl-5-benzyloxy-3-(2-tetrazol- 5-ylvinyl)indole is reduced to give N-benzyl-5-benzyloxy-3-(2-tetrazol-5-ylethyl)indole.

Example 65

N-methyl-N-phenethyl-2-[(5benzyloxy-3-dimethylamidomethyl)indol- 1-yl]acetamide

Step A: N-methyl-N-phenethyl-2-[(5-benzyloxy-3-carbomethoxymethyl)indol-1-yl]acetamide Following the procedure of Example 10 and using 5-benzyloxy-3-carbomethoxymethylindole in place of 5-benzyloxyindole-3-carboxaldehyde the product prepared is N-methyl-N-phenethyl-2-[(5-benzyloxy-3-carbomethoxymethyl)indol- 1-yl]acetamide.

Step B: N-methyl-N-phenethyl-2-[(5-benzyloxy-3-carboxymethyl)indol-1-yl]acetamide Following the procedure of Example 26, N-methyl-N-phenethyl-2-[(5-benzyloxy- 3-carbomethoxymethyl)indol-1-yl]acetamide is hydrolyzed to give N-methyl-N-phenethyl-2-[(5-benzyloxy-3-carboxymethyl)indol-1-yl] acetamide.

Step C: N-methyl-N-phenethyl-2-[(5-benzyloxy-3-dimethylamidomethyl)indol-1-yl]acetamide Following the procedure of Example 24, the acid from Step B is converted to the acid halide and treated with dimethylamine to obtain N-methyl-N-phenethyl-2-[(5-benzyloxy-3-dimethylamidomethyl)indol-1-yl]acetamide.

Example 66

N-methyl-N-phenethyl-2-[(5-(2-methylphenethylamino-2-oxo)ethoxy-3-diethylamidomethyl)indol-1-yl]acetamide Step A: N-methyl-N-phenethyl-2-[(5-(2-methylphenethylamino-2-oxo)ethoxy- 3-carbomethoxymethyl)indol-1-yl] acetamide Following the procedure of Example 10, 5-benzyloxyindole-3-carboxaldehyde is replaced with 5-[2-(N-methyl-N-phenethyl)amino-2-oxo]ethoxy- 3-carbomethoxy-methylindole to obtain N-methyl-N-phenethyl-2-[(5-(2-methylphenethylamino- 2-oxo)ethoxy-3-carbomethoxymethyl)indol-1-yl]acetamide.

Step B: N-methyl-N-phenethyl-2-[(5-(2-methylphenethylamino-2-oxo)ethoxy- 3-carboxymethyl)indol-1-yl]acetamide Following the procedure of Example 26, the ester from Step A is hydrolyzed to give N-methyl-N-phenethyl-2-[(5-(2-methylphenethylamino-2-oxo)ethoxy- 3-carboxymethyl)indol-1-yl]acetamide.

Step C: N-methyl-N-phenethyl-2-[(5-(2-methylphenethylamino-2-oxo)ethoxy- 3-diethylamidomethyl)indol-1-yl]acetamide Following the procedure of Example 24 the acid from Step B is convened to the acid halide and treated with diethylamine to obtain N-methyl-N-phenethyl- 2-[(5-(2-methylphenethylamino-2-oxo)ethoxy-3-diethylamidomethyl)indol-1-yl]acetamide.

Example 67

1-benzyl-3-carboxymethyl-5-[2-(N-methyl-N-phenethyl)amino- 2-oxo]ethoxyindole

Step A: 3-carbomethoxymethyl-5-[2-(N-methyl-N-phenethyl)amino-2-oxo]ethoxyindole Following the procedure of Example 2, 5-hydroxyindole is replaced by 3-carbomethoxymethyl-5-hydroxyindole to obtain 3-carbomethoxymethyl-5-[2-(N-methyl-N-phenethyl)amino- 2-oxo]ethoxyindole.

Step B: 1-benzyl-3-carbomethoxymethyl-5-[2-(N-methyl-N-phenethyl)-amino- 2-oxolethoxyindole Following the procedure of Example 10 and reacting benzyl bromide with 3-carbomethoxymethyl-5-[2-(N-methyl-N-phenethyl)amino-2-oxo]ethoxyindole the product prepared is 1-benzyl-3-carbomethoxymethyl-5-[2-(N-methyl-N-phenethyl)amino-2-oxo]ethoxyindole.

Step C: 1-benzyl-3-carboxymethyl-5-[2-(N-methyl-N-phenethyl)amino-2-oxo]ethoxyindole Following the procedure of Example 26 the ester from Step B is hydrolyzed to give 1-benzyl-3-carboxymethyl-5-[2-(N-methyl-N-phenethyl)amino- 2-oxo]ethoxyindole.

Example 68

N-methyl-N-phenethyl-2-[(4-benzyloxy-3-carboxy)indol-1-yl]acetamide

When 5-hydroxyindole in the procedure of Example 3 is replaced with 3-carbethoxy-4-hydroxyindole and the resulting 3-carbethoxy-4-benzyloxyindole is used in place of 5-benzyloxyindole-3-carboxaldehyde in the procedure of Example 10, then the product obtained is N-methyl-N-phenethyl-2-[(4-benzyloxy-3-carbethoxy)indol-1-yl]acetamide. When the latter is used in place of N-methyl-N-phenethyl-2-[(5-benzyloxy-3-formyl)indol-1-yl]acetamide then the product obtained is N-methyl-N-phenethyl-2-[(4-benzyloxy-3-carboxy)indol- 1-yl]acetamide. (m.p. 120°–125° C.)

Example 69

N-methyl-N-phenethyl-2-(4-benzyloxy-3-(2-trans-carboxy-2-methyl)vinylindol-1-yl)acetamide Step A: N-methyl-N-phenethyl-2-(4-benzyloxy-3-formylindol-1-yl acetamide To a suspension of sodium hydride (1.31 g, 80% suspension in mineral oil, 43.8 mM) in 65 ml of tetrahydrofuran (THF), cooled in an ice bath, is added dropwise a solution of 4-benzyloxyindole-3-carboxaldehyde (10.2 g, 39.8 mM) in 55 ml of THF. The mixture is stirred in the cooling bath for an additional 30 minutes; N-methyl-N-phenethyl-2-bromoacetamide (15.3 g, 59.7 mM) is then added. The resulting mixture is stirred at room temperature for 18 hours. Ethyl acetate and 50% brine is added and the layers are separated. The organic layer is washed with brine, dried over magnesium sulfate and concentrated in vacuo to give crude product as a beige oil. Purification on preparative HPLC (silica gel column, 20% ethyl acetate in methylene chloride) gives N-methyl-N-phenethyl- 2-(4-benzyloxy-3-formylindol-1-yl)acetamide. (m.p. 120°–122° C.)

Step B: N-methyl-N-phenethyl-2-(4-benzyloxy-3-(2-trans-carbethoxy-2-methyl)vinylindol- 1-yl)acetamide To a suspension of sodium hydride (0.259 g, 80% suspension in mineral oil, 8.64 mM) in 20 ml of THF, cooled in an ice bath, is added dropwise 1.87 g (7.85 mM) of triethyl 2-phosphonopropionate. The clear solution obtained in the reacting flask is stirred in the ice bath for an additional 10 minutes and a solution of N-methyl-N-phenethyl-2-(4-benzyloxy-3-formylindol-1-yl)acetamide (1.34 g, 3.14 mM) in 20 ml of THF added quickly. The cooling bath is removed and the reaction mixture stirred at room temperature for 18 hours. After quenching the reaction with a small amount of water, ethyl acetate and brine are added and the layers separated. The organic layer is washed with brine, dried (MgSO$_4$), and concentrated in vacuo to give a crude mixture as a brown oil. This material is purified by hplc on a silica gel column, using a one-to-one mixture of ethyl acetate and hexane as the solvent system, to give 0.89 g of the pure N-methyl-N-phenethyl-2-(4-benzyloxy-3-(2-trans-carbethoxy-2-methylvinyl)indol- 1-yl)acetamide. Also obtained from this hplc separation is 0.48 g of the cis-isomer and 0.05 g of a mixture of the cis and trans isomers confirmed by NMR.

Step C: N-methyl-N-phenethyl-2-(4-benzyloxy-3-(2-trans-carboxy-2-methyl)vinylindol- 1-yl)acetamide To a solution of N-methyl-N-phenethyl-2-(4-benzyloxy-3-(2-trans-carbethoxy- 2-methyl)vinylindol-1-yl)acetamide (0.7 g, 1.37 mM)in 0.3 ml of ethanol is added a solution of potassium hydroxide (0.261 g, 4.12 mM) in 7 ml of water. The resulting mixture is heated in an oil bath of 50° C. for four days. After cooling to room temperature, the bulk of ethanol is removed in vacuo. The concentrated mixture is dissolved in water and extracted with diethyl ether. The aqueous layer is acidified with 1N HCl to pH 6.5–7. The precipitate formed is extracted into ethyl acetate. The organic solution is washed with brine, dried (MgSO$_4$) and concentrated in vacuo) to give N-methyl-N-phenethyl-2-(4-benzyloxy- 3-(2-trans-carboxy-2-methyl)vinylindol-1-yl) acetamide. (m.p. 199°–201° C.).

Example 70

N-methyl-N-phenethyl-2-5-benzoylamide-3-(2-carboxyethyl)indol-1-yl]acetamide

Step A: N-methyl-N-phenethyl-2-(5-nitro-3-carboxaldehydeindol-1-yl)acetamide

To a mixture of sodium hydride (1.9 g, 78.9 mmol) in anhydrous tetrahydrofuran (200 ml) at 0° C. is added portionwise 5-nitro-3-carboxaldehydeindole (15.0 g, 78.9 mmol). The reaction is allowed to stir for 30 minutes. N-methyl-N-phenethyl-2-bromoacetamide (20.2 g, 78.9 mmol) is added and the reaction stirred for 16 hours and then heated at reflux. After allowing to cool the solid is filtered off, the solvent is removed and the residue is crystallized from chloroform/hexane to give N-methyl-N-phenethyl-2-(5-nitro-3-carboxaldehydeindol-1-yl)acetamide. (m.p. 200° C.)

Step B: N-methyl-N-phenethyl-2-[5-nitro-3-(t-butyl-2-carboxyvinyl)indol-1-yl]acetamide To a chilled solution of t-butyl diethylphosphono-acetate (5.4 g, 21.4 mmol) in dimethylformamide (15 ml) sodium hydride (0.51 g, 21.4 mmol) is added portionwise. The reaction is allowed to come to ambient temperature and stirred for 1 hour. The aldehyde, N-methyl-N-phenethyl-2-(5-nitro-3-carboxaldehydeindol-1-yl)acetamide (5.2 g, 14.2 mmol) is added portionwise. After 1½ hours the reaction is poured into water (600 ml) and extracted with ethyl acetate (3×10). The ethyl acetate layer is dried ($Na_2SO_4$) and the solvent is removed. This gives a red oil which is crystallized for hexane/ethyl acetate to give N-methyl-N-phenethyl-2-[5-nitro-3-(t-butyl-2-carboxyvinyl)indol- 1-yl]acetamide. (m.p. 140°–143° C.)

Step C: N-methyl-N-phenethyl-2-[5-benzoylamide-3-t-butyl-2-carboxyethyl)indol-1-yl]acetamide A mixture of N-methyl-N-phenethyl-2-[5-nitro-3-(t-butyl-2-carboxyvinyl)indol-1-yl]acetamide (0.9 g, 1.9 mmol), tetrahydrofuran (30 ml), ethanol (30 ml), and palladium on carbon (10%, 0.2 g) is shaken under hydrogen (45 psi). After 4 hours the mixture is filtered through celite and the solvent is removed. The residue is added to a solution of N-benzoylimidazole (5.8 mmol) in tetrahydrofuran (20 ml). After 16 hours the solvent is removed and methanol (50 ml) is added. The solution is allowed to stand for 1½ and the methanol is removed. The oil is chromatographed using silica gel and an ethylacetate/hexane 1:1 solution until the methyl benzoate is removed.

The solvent is changed to ethylacetate:hexane 2:1. This gives crude product which is crystallized from $CHCl_3$/ether/hexane to give N-methyl-N-phenethyl- 2-[5-benzoyl-amide-3-(t-butyl-2-carboxyethyl)indol-1-yl]acetamide as a white solid. (m.p. 158°–159° C.)

Step D: N-methyl-N-phenethyl-2-[5-1benzoylamide-3-(2-carboxyethyl)indol-1-yl]acetamide A solution of (0.25 g, 0.46 mmol) of N-methyl-N-phenethyl-2-[5-benzoyl-amide-3-(t-butyl-2-carboxyethyl)indol-1-yl]acetamide is dissolved in trifluoroacetic acid/methylene chloride (1:1, 6 ml). After stirring for 3 hours the solvent is removed and the residue is dissolved in a small amount of ethanol. Ethylether is added and the fluffy tan solid is filtered to give N-methyl-N-phenethyl- 2-[5-benzoylamide-3-(2-carboxyethyl)indol-1-yl]acetamide. (m.p. 9°–222° C.)

Example 71

1-[(N-methyl-N-(2-phenethyl)-2-acetamido]-6-benzyloxy-3-naphthoic acid

Step A: 3-carbomethoxy-4-(3methoxyphenyl)-3-butenoic acid

To a refluxing suspension of 15.71 g (140 mmol, 1.4 eq) of potassium t-butoxide in 50 ml of t-butylalcohol is dropped in a mixture of 12.17 (100 mmol) of 3-methoxybenzaldehyde and 15.70 ml (120 mmol, 1.2 eq) of dimethyl succinate dissolved in 20 ml of t-butylalcohol. The mixture is refluxed for 3 hours, concentrated in vacuo, acidified to pH ~1 using 1N HCl, and extracted with ethylacetate. The organics are dried ($MgSO_4$) and concentrated in vacuo to give 3-carbomethoxy-4-(3-methoxyphenyl)-3-butenoic acid in the form of a yellow oil which is used directly in the next step.

Step B: 3-carbomethoxy-4-(3-methoxyphenyl)butanoic acid

A solution of 21.1 g (84 mmol) of 3-carbomethoxy-4-(3-methoxyphenyl)-3-butenoic acid in 100 ml of acetic acid with 2.11 g of 10% Pd on carbon is shaken under $H_2$ atmosphere until $H_2$ uptake ceases (approximately 4 hours). This is filtered through celite and the filtrate concentrated in vacuo several times from toluene to afford 17.6 g of 3-carbomethoxy-4-(3-methoxyphenyl)butanoic acid in the form of a yellow oil which is used directly in the next step.

Step C: 3-carbomethoxy-6-benzyloxy-1-tetralin

A solution of 14 g (55.57 mmol) of 3-carbomethoxy-4-(3-methoxyphenyl)butanoic acid in 200 ml of $CH_2Cl_2$ is refluxed for 18 hours with 8.1 ml (110.99 mmol, 2 eq) of $SOCl_2$ and 2 drops of DMF. After concentration in vacuo several times from $CH_2Cl_2$, this is dissolved in 50 ml of 1,2-dichloroethane and dropped into a suspension of 22.19 g (166.49 mmol, 3 eq) of $AlCl_3$ in 200 ml of 1,2-dichloroethane at 25° C. After refluxing for 3 hours, the cooled mixture is quenched with $H_2O$, acidified to pH ~1 using 1N HCl, and extracted with $CH_2Cl_2$. The organics are dried ($MgSO_4$) and concentrated in vacuo. This is dissolved in 50 ml of DMF and heated at 60° C. for 18 hours with 6 ml (47.68 mmol, 1.5 eq) of benzylbromide and 6.6 g (47.68 mmol, 1.5 eq) of $K_2CO_3$. The mixture is partitioned between ethyl acetate and $H_2O$. The organics are dried ($MgSO_4$) and concentrated in vacuo. This is purified by flash silica gel chromatography using 20% ethyl acetate in hexanes as an eluent to give 3.0 g of 3-carbomethoxy-6-benzyloxy-1-tetralin in the form of a pale yellow crystalline solid. (m.p. 139°–140° C.)

Step D: 3-carbomethoxy-6-benzyloxy-1-naphthol

A solution of 3.4 g (10.96 mmol) of 3-carbomethoxy-6-benzyloxy-1-tetralin and 3.5 g (10.96 mmol) of pyridinium bromideperbromide in 30 ml of acetic acid is heated at 60° C. for 1 hour. The mixture is partitioned between $Et_2O$ and $H_2O$. The organics are dried ($MgSO_4$) and concentrated in vacuo. The residue in 20 ml of DMSO is stirred for 1 hour with 3.69 g (32.87 mmol, 3 eq) of potassium t-butoxide at 25° C. The mixture is acidified to pH 1 using 1N HCl, then partitioned between ethyl acetate and $H_2O$. The organics are dried ($MgSO_4$) and concentrated in vacuo. To the residue in 25 ml of $CH_2Cl_2$ is added 1.95 g (12.05 mmol, 1.1 eq) of carbonyl diimidazole and a catalytic amount of DMAP which is stirred at 25° C. for 0.5 hours. This is then stirred for 18 hours with 2 ml of MeOH. This is concentrated in vacuo and partitioned between ethyl acetate and 1N HCl. The organics are dried ($MgSO_4$) and concentrated in vacuo. This is purified by flash silica gel chromatography using 15% ethyl acetate in hexanes as an eluent affords 0.50 g of 3-carbomethoxy- 6-benzyloxy-1-naphthol in the form of a white crystalline solid, (m.p. 179°–180° C.)

Step E: 1-trifluoromethylsulfonyloxy-3-carbomethoxy-6-benzyloxynaphthalene

To 0.65 g (2.11 mmol) of 3-carbomethoxy-6-benzyloxy-1-naphthol in 20 ml of pyridine at 0° C. is added 0.43 ml (2.5 mmol, 1.2 eq) of trifluoromethanesulfonic anhydride which is then stirred for 18 hours at 25° C. The mixture is concentrated in vacuo and partitioned between ethyl acetate and 1N HCl. The organics are dried ($MgSO_4$) and concentrated in vacuo. Purification by flash silica gel chromatography using 7% ethyl acetate in hexanes as an eluent affords 0.5 g of 1-trifluoromethylsulfonyloxy-3-carbomethoxy-6-benzyloxynaphthalene in the form of a clear oil which is used directly in the next step.

Step F: 1-vinyl-3-carbomethoxy-6-benzyloxynaphthalene

A solution of 0.5 g (1.4 mmol) of 1-trifluoromethylsulfonyloxy-3-carbomethoxy- 6-benzyloxynaphthalene in 20 ml of DMF is stirred at 25° C. for 18 hours with 0.18 g (4.27 mmol, 3 eq) of LiCl, 0.46 ml (1.57 mmol, 1.1 eq) of vinyl-tributyltin and 0.019 g (0.03 mmol, 0.02 eq) bis(triphenyl-phosphine) palladium (II) chloride. The mixture is partitioned between ethyl acetate and 1N HCl. The organics are dried ($MgSO_4$) and concentrated in vacuo. Purification by flash silica gel chromatography using 5% ethyl acetate in hexanes as an eluent affords 0.3 g of 1-vinyl-3-carbomethoxy-6-benzyloxynaphthalene in the form of a yellow oil which is used directly in the next step.

Step G: 1-hydroxyethyl-3-carbomethoxy-6-benzyloxynaphthalene

A solution of 0.3 g (0.9 mmol) of 1-vinyl-3-carbomethoxy-6benzyloxynaphthalene and 0.9 ml (0.9 mmol) of 1.0M $BH_3$.THF complex in 15 ml of THF is stirred at 25° C. for 2 hours. To this is added 1 ml of $H_2O$, 1 ml of 1N NaOH and 1 ml of 30% $H_2O_2$ which is then stirred at 25° C. for 2 hours. The mixture is acidified to pH ~1 using 1N HCl and extracted with ethyl acetate. The organics are dried ($MgSO_4$) and concentrated in vacuo. Purification by flash silica gel chromatography using 15% ethyl acetate in hexanes as an eluent affords 0.08 g of 1-hydroxyethyl-3-carbomethoxy-6-benzyloxynaphthalene in the form a yellow oil which is used directly in the next step.

Step H: 3-carbomethoxy-6-benzyloxy-1-naphthyl acetic acid

To a solution of 0.08 g (0.24 mmol) of 1-hydroxyethyl-3-carbomethoxy-6-benzyloxynaphthalene in 10 ml of acetone at 0° C. is added Jones reagent until a green precipitate forms. After stirring at 0° C. for 10 minutes, the mixture is partitioned between ethyl acetate and $H_2O$. The organics are dried ($MgSO_4$) and concentrated in vacuo to afford 0.081 g of 3-carbomethoxy-6-benzyloxy-1-naphthyl acetic acid in the form of a light tan solid which is used directly in the next step.

Step I: 1-[(N-methyl-N-(2-phenethyl)-2-acetamido]-3-carbomethoxy-6-benzyloxynaphthalene A solution of 0.051 g (0.23 mmol) of 3-carbomethoxy-6-benzyloxy-1-naphthyl acetic acid, 0.041 g (0.25 mmol, 1.1 eq) of carbonyl diimidazole and a catalytic amount of DMAP is stirred at 25° C. for 1 hour in 15 ml of $CH_2Cl_2$. To this is added 0.037 ml (0.25 mmol, 1.1 eq) of N-methyl-N-phenethylamine which is then stirred at 25° C. for 18 hours. The mixture is concentrated in vacuo, then partitioned between ethyl acetate and 1N HCl. The organics are dried ($MgSO_4$) and concentrated in vacuo. Purification by thick layer prep plate chromatography developed in 10% acetone in hexanes affords 0.1 g of 1-[(N-methyl-N-(2-phenethyl)-2-acetamido]-3-carbomethoxy-6-benzyloxynaphthalene in the form of a yellow oil which is used directly in the next step.

Step J: 1-[(N-methyl-N-(2-phenethyl-2-acetamido]-6-benzyloxy-3-naphthoic acid

A solution of 0.07 g (0.15 mmol) of 1-[(N-methyl-N-(2-phenethyl)-2-acetamido]-3-carbomethoxy-6-benzyloxynaphthalene and 0.31 g (0.75 mmol, 5 eq) of lithium hydroxide monohydrate in 20 ml of a 1:1:1 mixture of $THF:H_2O:MEOH$ is stirred at 25° C. for 10 hours. The mixture is acidified to pH ~1 using 1N HCl and extracted with ethyl acetate. The organics are dried ($MgSO_4$) and concentrated in vacuo. The residue is triturated with $ET_2O$/hexanes and the solid filtered off to afford 0.035 g of 1-[(N-methyl-N-(2-phenethyl)- 2-acetamido]-6-benzyloxy-3-naphthoic acid in the form of a white crystalline solid. (m.p. 76°–79° C.)

Example 72

N-methyl-N-phenethyl-2-[5-benzyloxy-3-(2-carbethoxy-2-methylvinyl)indol-1-yl]acetamide N-methyl-N-phenethyl-2-[5-benzyloxy-3-(2-(E)-carbethoxy-2-methylvinyl)indol-1-yl]acetamide N-methyl-N-phenethyl-2-[5-benzyloxy-3-(2-(Z)-carbethoxy-2-methylvinyl)indol-1-yl]acetamide Following the procedure of Example 34, N-methyl-N-phenethyl-2-[5-benzyloxy- 3-(2-carbethoxy-2-methylvinyl)indol-1-yl]acetamide is prepared. (m.p. 128°–130° C.)

This substance is further purified on a silica gel flash column, eluting with a solvent system of 2% ethyl acetate in methylene chloride to give N-methyl-N-phenethyl-2-[5-benzyloxy-3-(2-(E)-carbethoxy-2-methylvinyl)-indol- 1-yl] acetamide and N-methyl-N-phenethyl-2-[5-benzyloxy-3-(2-(Z)-carbethoxy- 2-methylvinyl)indol-1-yl]acetamide. NMR confirms these structures.

Example 73

N-methyl-N-phenethyl-2-[4-benzyloxy-3-(2-carboxy-2-ethylvinyl) indol-1-yl]acetamide When N-methyl-N-phenethyl-2-[5-benzyloxy-3-(2-carboethoxyvinyl)-indol- 1-yl]acetamide in the procedure of Example 23 is replaced with N-methyl-N-phenethyl- 2-[4-benzyloxy-3-(2-carboethoxyvinyl)indol-1-yl]acetamide then the product prepared is N-methyl-N-phenethyl-2-[4-benzyloxy-3-(2-carboxyvinyl)indol- 1-yl]acetamide as a white powder. (m.p. 170°–174° C.)

Example 74

5-benzyloxy-3-(3-carbmethoxybenzoyl)indole

To a solution 5-benzyloxyindole (2.23 g, 10 mmol) in 5 ml of tetrahydrofuran (THF), cooled in an external ice bath, is added dropwise with stirring 6.15 ml of a 2 molar solution of methyl magnesium bromide in diethyl ether. The resulting mixture is stirred for an additional 15 minutes in the ice bath and a solution of 3-carbmethoxybenzoyl chloride in 10 ml of THF is added dropwise. The cooling bath is removed and the reaction mixture is stirred at room temperature for 18 hours. Water is then added, followed by ethyl acetate. The layers are separated. The organic layer is dried ($MgSO_4$) and concentrated in vacuo. The residue obtained is purified by a silica gel column, eluting with a solvent system of 25% ethyl acetate in hexane to give 5-benzyloxy-3-(3-carbomethoxybenzoyl)indole. NMR confirms this structure.

Example 75

4-benzyloxy-3-carboethoxyphenylmethylindole

When 5-benzyloxyindole and 3-carbomethoxybenzoyl chloride in the procedure of Example 74 are replaced by 4-benzyloxyindole and ethyl 2-bromophenylacetate, respectively, then the compound prepared is 4-benzyloxy-3-carboethoxyphenylmethylindole as an off-white powder. (m.p. 126°–128° C.)

Example 76

5-benzyloxy-3-(3-carboethoxy-2-propenyl)indole

When 3-carbmethoxybenzoyl chloride in the procedure of Example 74 is replaced by ethyl 4-bromocrotonate then the compound prepared is 5-benzyloxy-3-(3-carboethoxy-2-propenyl)indole which is a beige oil. NMR confirms this structure.

Example 77

N-methyl-N-phenethyl-2-[5-benzyloxy-3-(3-carbomethoxybenzoyl)indol-1-yl]acetamide When 5-benzyloxyindole-3-carboxaldehyde in the procedure of Example 10 is replaced by 5-benzyloxy-3-(3-carbomethoxybenzoyl)indole, then the compound prepared is N-methyl-N-phenethyl-2-[5-benzyloxy-3-(3-carbomethoxybenzoyl)indol-1-yl]acetamide. This compound is recrystallized from ethyl acetate to give a beige crystal. (m.p. 224°–230° C.)

Example 78

N-methyl-N-phenethyl-2-(4-benzyloxy-3-carboethoxyphenylmethylindol-1-yl]acetamide When 5-benzyloxyindole-3-carboxaldehyde in the procedure of Example 10 is replaced by 4-benzyloxy-3-carboethoxyphenylmethylindole, then the compound prepared is N-methyl-N-phenethyl-2-(4-benzyloxy-3-carboethoxyphenylmethylindol-1-yl)acetamide.

Example 79

N-methyl-N-phenethyl-2-[-5-benzyloxy-3-(3-carboethoxy-2-propenyl)indol-1-yl]acetamide When 5-benzyloxyindole-3-carboxaldehyde in the procedure of Example 10 is replaced by 5-benzyloxy-3-(3-carboethoxy-2-propenyl)indole, then the compound prepared is N-methyl-N-phenethyl-2-[5-benzyloxy-3-(3-carboethoxy-2-propenyl)indol-1-yl]acetamide. NMR confirms this structure.

Example 80

N-methyl-N-phenethyl-2-5-benzyloxy-3-(3-carboxybenzoyl)indol-1-yl]acetamide

N-methyl-N-phenethyl-2-[(4-benzyloxy-3-(1-carboxy-1-phenyl)methyl)indol-1-yl]acetamide
N-methyl-N-phenethyl-2-[5-benzyloxy-3-(3-carboxy-2-propenyl)indol-1-yl]acetamide In a procedure similar to that described in Example 23, N-methyl-N-phenethyl- 2-[5-benzyloxy-3-(carboethoxybenzoyl)indol-1-yl]acetamide is hydrolyzed to N-methyl-N-phenethyl-2-[5-benzyloxy-3-(carboxybenzoyl)indol-1-yl] acetamide as a beige powder. (m.p. 224°–230° C.)

Similarily, N-methyl-N-phenethyl-2-(4-benzyloxy-3-(1-carboethoxy-1-phenyl)methylindol- 1-yl)acetamide is hydrolyzed to N-methyl-N-phenethyl-2-(4-benzyloxy-3-(1-carboxy-1-phenyl)methylindol-1-yl)acetamide as a white crystal. (m.p. 201°–203° C.)

N-methyl-N-phenethyl-2-[5-benzyloxy-3-(3-carboethoxy-2-propenyl)-indol- 1-yl]acetamide is hydrolyzed to N-methyl-N-phenethyl-2-[5-benzyloxy-3-(3-carboxy-2-propenyl)indol-1-yl]acetamide as an orange powder. (m.p. 150°–155° C. (dec.))

Example 81

5-phenoxyindole-3-carboxaldehyde

When N-methyl-N-phenethyl-2-(5-indolyloxy)acetamide in the procedure of Example 6 is replaced with 5-phenoxyindole, then the product obtained is 5-phenoxyindole-3-carboxaldehyde. NMR confirms this structure.

Example 82

5-phenylindole-3-carboxaldehyde

When N-methyl-N-phenethyl-2-(5-indolyloxy)acetamide in the procedure of Example 6 is replaced with 5-phenylindole, then the product prepared is 5-phenylindole-3-carboxaldehyde. NMR confirms this structure.

Example 83

N-methyl-N-phenethyl-2-[(3-formyl-5-phenoxy)indol-1-yl]acetamide

When 5-benzyloxyindole-3-carboxaldehyde in the procedure of Example 10 is replaced by 5-phenoxyindole-3-carboxaldehyde, then the compound prepared is N-methyl-N-phenethyl-2-[(3-formyl-5-phenoxy)indol-1-yl]acetamide. NMR confirms this structure.

Example 84

Following the procedure of Example 10 the following compounds may be prepared:
N-methyl-N-phenethyl-2-[(3-formyl-5-phenyl)indol-1-yl]acetamide;
N-methyl-N-phenethyl-2-[(4-bromo-3-formyl)indol-1-yl] acetamide; and
N-methyl-N-phenethyl-2-[3-formyl-4-(2-phenylvinyl)indol-1-yl]acetamide.
NMR confirms these structures.

Example 85

4-(2-phenylvinyl)indole

When indole-4-carboxaldehyde is treated with the anion prepared from 2.5 molar equivalent of diethyl benzylphosphonate and sodium hydride, in a procedure similar to that described in Example 22, then the product prepared is 4-(2-phenylvinyl)indole. NMR confirms this structure.

Example 86

4-(2-phenylvinyl)indole-3-carboxaldehyde

When 4-(2-phenylvinyl)indole is used in Example 6 the product prepared is 4-(2-phenylvinyl)indole-3-carboxaldehyde. NMR confirms this structure.

Example 87

Following the procedure of Example 22 the following compounds may be prepared:

N-methyl-N-phenethyl-2-[3-(2-carbethoxyvinyl)-5-phenoxyindol-1-yl]acetamide;

N-methyl-N-phenethyl-2-[3-(2-carbethoxyvinyl)-5-phenylindol-1-yl]acetamide;

N-methyl-N-phenethyl-2-[4-bromo-3-(2-carbethoxyvinyl)indol-1-yl]acetamide; and

N-methyl-N-phenethyl-2-[3-(2-carbethoxyvinyl)-4-(2-phenylvinyl)indol-1-yl]acetamide.

NMR confirms these structures.

Example 88

Following the procedure of Example 23 the following compounds may be prepared.

N-methyl-N-phenethyl-2-[3-(2-carboxyvinyl)-5-phenoxyindol-1-yl]acetamide;

N-methyl-N-phenethyl-2-[3-(2-carboxyvinyl)-5-phenylindol-1-yl]acetamide;

N-methyl-N-phenethyl-2-[4-bromo-3-(2-carboxyvinyl)indol-1-yl]acetamide; and

N-methyl-N-phenethyl-2-[3-(2-carboxyvinyl)-4-(2-phenylvinyl)indol-1-yl]acetamide.

NMR confirms these structures.

Example 89

Following the procedures of Examples 1–88 the following compounds may be prepared.

4-[(N-methyl-N-phenethyl)carbamoylmethyl]-1-benzyloxy-2-naphthoic acid (m.p. 55°–60° C.)

4-[(N-methyl-N-phenethyl)carbamoylmethyl]-8-benzyloxy-2-naphthoic acid (m.p. 181°–183° C.)

4-[(N-methyl-N-phenethyl)carbamoylmethyl]-8-phenyl-2-naphthoic acid (m.p. 175°–177° C.)

4-[(N-methyl-N-phenethyl)carbamoylmethyl]-8-phenyl-2-(2-carboxy)vinylnaphthalene (m.p. 159° C.(dec.))

2-(2-carboxy)ethyl-4-[(N-methyl-N-phenethyl)carbamoylmethyl]-8-phenyl-naphthalene (m.p. 79°–80° C.)

8-benzyloxy-2-(2-carboxy)vinyl-4-[(N-methyl-N-phenethyl)carbamoylmethyl]naphthalene (m.p. 168°–170° C.)

5-benzyloxy-3-(4-carboxy-1,2-butadienyl)-1-[(N-methyl-N-phenethyl)carbamoylmethyl]naphthalene (m.p. 91°–100° C.(dec.))

5-benzyloxy-3-(4-carboxybutyl)-1-[(N-methyl-N-phenethyl)carbamoylmethyl]naphthalene (m.p. 110°–113° C.)

1-[(N-methyl-N-phenethyl)carbamoylmethyl]-3-(2-methyl-2-carboxy)vinyl-5-benzyloxynaphthalene (m.p. 172°–176° C.)

5-benzyloxy-3-[(2-carboxy-2-ethyl)vinyl]-1-[(N-methyl-N-phenethyl)carbamoylmethyl]naphthalene (m.p. 77°–79° C.)

4-[(N-methyl-N-phenethyl)carbamoylmethyl]-8-(2-quinoline-2-ylmethoxy)-2-naphthoic acid (m.p. 184°–186° C.)

4-[(N-methyl-N-phenethyl)carbamoylmethyl]-8-(naphth-2-ylmethoxy)-2-naphthoic acid (m.p. 174°–176° C.)

4-[(N-methyl-N-phenethyl)carbamoylmethyl]-8-(pyridine-3-ylmethoxy)-2-naphthoic acid (m.p. 207°–209° C.)

5-benzyloxy-3-carboxy-1-[(N2hydroxy-N-phenethyl)carbamoylmethyl]-naphthalene (m.p. 195°–202° C.)

We claim:

1. A compound of the formula

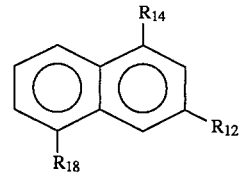

where:

$R_{12}$ is $$-(CH_2)_d-D-(CH_2)_e-E$$

where D is a chemical bond, O, —CH$_2$ or —(CH=CH)$_x$ where x is 1 or 2 and E is —COOR' or tetrazolyl where R' is hydrogen or C$_{1-6}$ alkyl;

$R_{14}$ is

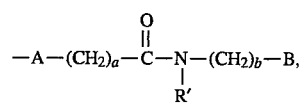

where A is —CH$_2$ or O; B is phenyl or substituted phenyl where the substituents are C$_{1-6}$ alkyl, halo C$_{1-6}$ alkyl, C$_{1-6}$ alkoxy or halo and R' is hydrogen or C$_{1-6}$ alkyl;

$R_{18}$ is $$-(CH_2)_f-(CH_2)_g-G$$

where F is O or —CH$_2$ and G is phenyl or substituted phenyl where the substituents are C$_{1-6}$ alkyl, halo C$_{1-6}$ alkyl, C$_{1-6}$ alkoxy or halo; and a, b, d, e, f and g are independently 0–4; or a pharmaceutically acceptable salt thereof.

2. A compound according to claim 1 which is 4-[(N-methyl-N-phenethyl)-carbamoylmethyl]- 8-benzyloxy-2-naphthoic acid or a pharmaceutically acceptable salt thereof.

3. A compound according to claim 1 which is 4-[(N-methyl-N-phenethyl)-carbamoylmethyl]- 8-phenyl-2-naphthoic acid or a pharmaceutically acceptable salt thereof.

4. A compound according to claim 1 which is 4-[(N-methyl-N-phenethyl)-carbamoylmethyl]- 8-phenyl-2-(2-carboxy)vinylnaphthalene or a pharmaceutically acceptable salt thereof.

5. A compound according to claim 1 which is 2-(2- carboxy)ethyl-4[-(N-methyl-N-phenethyl)carbamoylmethyl]- 8-phenylnaphthalene or a pharmaceutically acceptable salt thereof.

6. A compound according to claim 1 which is 8-benzyloxy-2-(2-carboxy)vinyl- 4-[(N-methyl-N-phenethyl)carbamoylmethyl]naphthalene or a pharmaceutically acceptable salt thereof.

* * * * *